United States Patent
Tamai et al.

(10) Patent No.: US 11,492,334 B2
(45) Date of Patent: Nov. 8, 2022

(54) METHODS FOR PRODUCING NITROSO COMPOUND AND QUINOXALINE COMPOUND

(71) Applicant: Kumiai Chemical Industry Co., Ltd., Tokyo (JP)

(72) Inventors: Ryuji Tamai, Tokyo (JP); Yukio Uchida, Tokyo (JP); Fumiaki Takabe, Tokyo (JP); Akira Kato, Tokyo (JP); Ryo Maruyama, Tokyo (JP); Ryo Kobayashi, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 17/253,823

(22) PCT Filed: Jan. 31, 2020

(86) PCT No.: PCT/JP2020/003687
§ 371 (c)(1),
(2) Date: Dec. 18, 2020

(87) PCT Pub. No.: WO2020/158925
PCT Pub. Date: Aug. 6, 2020

(65) Prior Publication Data
US 2021/0253539 A1    Aug. 19, 2021

(30) Foreign Application Priority Data
Jan. 31, 2019  (JP) .............................. JP2019-014969

(51) Int. Cl.
*C07D 241/44*    (2006.01)
*C07C 213/08*    (2006.01)

(52) U.S. Cl.
CPC .......... *C07D 241/44* (2013.01); *C07C 213/08* (2013.01); *C07C 2601/16* (2017.05)

(58) Field of Classification Search
CPC .................................................. C07D 241/44
USPC ........................................................ 544/354
See application file for complete search history.

(56) References Cited

U.S. PATENT DOCUMENTS

| | | |
|---|---|---|
| 2010/0197674 A1 | 8/2010 | Tamai et al. |
| 2014/0336415 A1 | 11/2014 | Ito et al. |

FOREIGN PATENT DOCUMENTS

| | | |
|---|---|---|
| JP | 201870520 A | 5/2018 |
| WO | 2009016841 A1 | 2/2009 |
| WO | 2013089002 A1 | 6/2013 |

OTHER PUBLICATIONS

Wrobel, Synlett (2007), (10), 1525-1528.*
Veith, Zeitschrift fuer Anorganische und Allgemeine Chemie (2010), 636(12), 2262-2275.*
Wrobel et al., "Simple Synthesis of N-Aryl-2-nitrosoanilines in the Reaction of Nitroarenes with Aniline Anion Derivatives", Synthesis, 2010, pp. 3865-3872, No. 22.
Demidov et al., "SNH Arylamination of Nitroquinolines: Access to Nitro and Nitroso Derivatives of Arylaminoquinolines", Chemistry of Heterocyclic Compounds, 2018, pp. 875-886, vol. 54, No. 9.
Trawczynski et al., "Expedient Synthesis of 6-Acylindolo[1,2-a]quinoxalines", Synlett, 2015, pp. 1352-1356, vol. 26.
Wrobel et al., "Reactivity and Substituent Effects in the Cyclization of N-aryl-2-nitrosoanilines to Phenazines", Tetrahedron, 2017, pp. 3147-3152, vol. 73.
Wrobel et al., "A Two-Step Oxidative Aromatic Substitution of Hydrogen as a Convenient Way to 2-nitrodiarylamines", Tetrahedron, 2016, pp. 8252-8260, vol. 72.

* cited by examiner

*Primary Examiner* — Nizal S Chandrakumar
(74) *Attorney, Agent, or Firm* — The Webb Law Firm

(57) ABSTRACT

A method for producing a nitroso compound of the following formula (3), comprising reacting a compound of the following formula (1) with a compound of the following formula (2) by using a tertiary alcohol and a base.

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy.

15 Claims, No Drawings

METHODS FOR PRODUCING NITROSO COMPOUND AND QUINOXALINE COMPOUND

CROSS-REFERENCE TO RELATED APPLICATIONS

This application is the United States national phase of International Application No. PCT/JP2020/003687 filed Jan. 31, 2020, and claims priority to Japanese Patent Application No. 2019-014969 filed Jan. 31, 2019, the disclosures of which are hereby incorporated by reference in their entirety.

BACKGROUND OF THE INVENTION

Technical Field

The present invention relates to a method for producing a compound of the following formula (3), which is a nitroso compound.

[Formula 1]

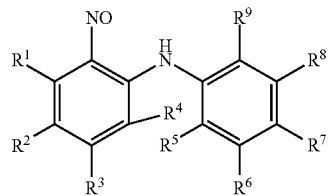

(3)

wherein $R^1$, $R^2$, $R^3$, $R^4$, $R^5$, $R^6$, $R^7$, $R^8$, and $R^9$ are as described later.

The present invention also relates to a method for producing a compound of the following formula (5), which is a quinoxaline compound.

[Formula 2]

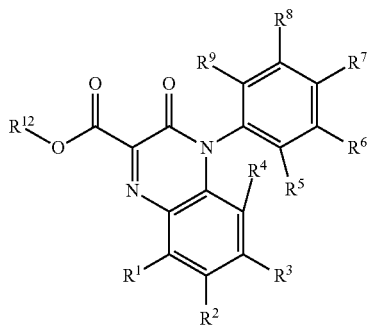

(5)

wherein $R^1$, $R^2$, $R^3$, $R^4$, $R^5$, $R^6$, $R^7$, $R^8$, $R^9$, and $R^{12}$ are as described later.

Background Art

The nitroso compound of the formula (3) (hereinafter simply referred to as the compound of the formula (3)) and the quinoxaline compound of the formula (5) (hereinafter simply referred to as the compound of the formula (5)) are useful as intermediates for the production of physiologically active organic compounds, such as agrochemicals and medicines, and the like. In WO2009/016841 (Patent Literature 1), useful herbicides are described. Among them, compound No. II-62 and compound No. II-194 are excellent herbicides. Particularly, compound No. II-194, that is, Fenquinotrione, is known as a herbicide having an extremely excellent weeding effect and high safety for paddy rice.

In addition, WO2009/016841 (Patent Literature 1) also discloses that the compound of the formula (5) is useful as an intermediate for the production of herbicides (see specifically, for example, Example 6).

WO2013/089002 (Patent Literature 2) discloses the production method as shown in the diagram below (see Examples 1, 3, 19, 20 to 23, and the like).

[Formula 3]

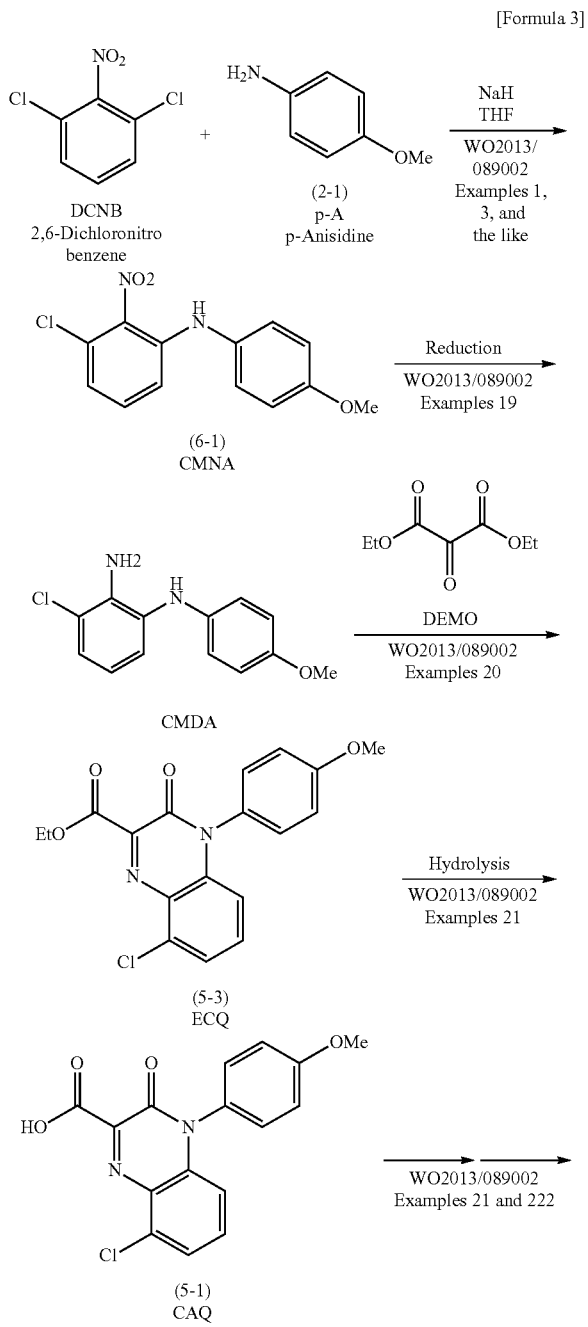

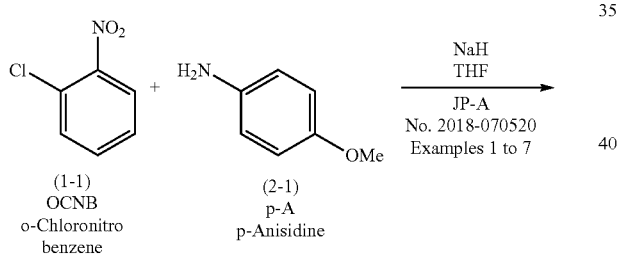

Fenquinotrione
(herbicide)

As seen from the above diagram, the method described in WO2013/089002 (Patent Literature 2) requires three steps in order to produce the compound of the formula (5), specifically the compound of the formula (5-3), from 2,6-dichloronitrobenzene. Therefore, a production method having a fewer number of steps has been desired. In addition, 2,6-dichloronitrobenzene and ketomalonic acid diester (for example, DEMO in the above diagram) are less easily available, and more easily available raw materials have been desired.

On the other hand, Japanese Patent Laid-Open No. 2018-70520 (Patent Literature 3) discloses that 3-chloro-N-(4-methoxyphenyl)-2-nitrosoaniline (3-1) can be produced by reacting 2-chloronitrobenzene (1-1) with p-anisidine (2-1). Further, in this literature, it is reported that the compound of the formula (5-3) can be produced from 3-chloro-N-(4-methoxyphenyl)-2-nitrosoaniline (3-1). This method is shown in the diagram below.

[Formula 4]

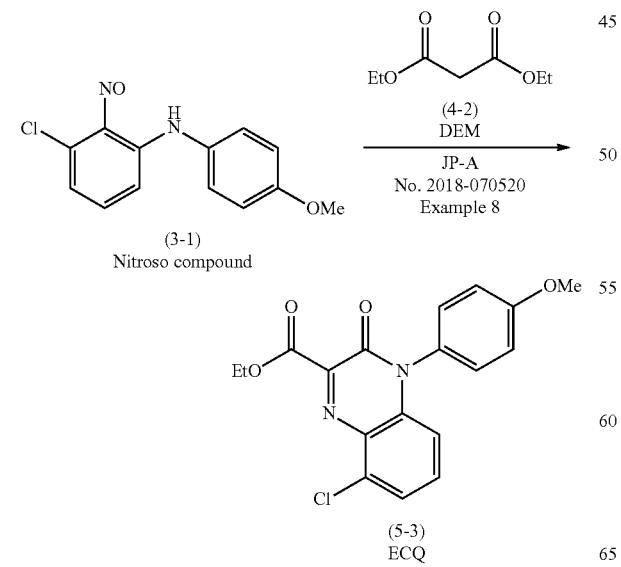

Compared with the method of WO2013/089002 (Patent Literature 2), the compound of the formula (5-3) can be produced using more easily available raw materials in the method of Japanese Patent Laid-Open No. 2018-70520 (Patent Literature 3). But the method described in Japanese Patent Laid-Open No. 2018-70520 (Patent Literature 3) requires 2 equivalents to 3 equivalents of p-anisidine (2-1) based on 2-chloronitrobenzene (1-1), and therefore decreasing the amount of p-anisidine used has been desired. Further, the conditions of the Examples of this method include a low temperature of −70° C. to 0° C.

Synlett (2015), 1352-1356 (Non Patent Literature 1) discloses that the compound of the formula (3) can be produced in a high yield. But this method requires a low temperature of −70° C. to −30° C. A specific example is shown in the diagram below.

[Formula 5]

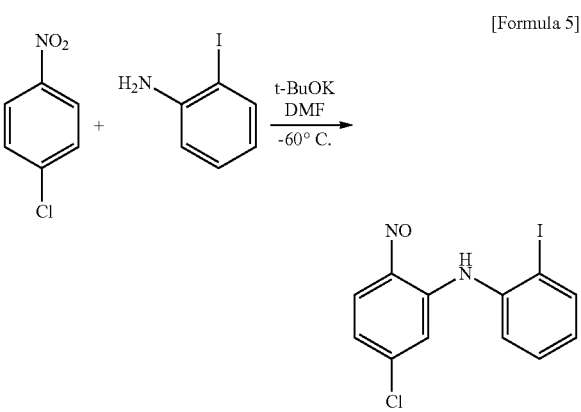

Further, Tetrahedron (2016), 8252-8260 (Non Patent Literature 2) discloses that the compound of the formula (3) can be produced in a moderate yield. In this literature, a method involving starting the reaction at −65° C. and then increasing the temperature to room temperature is reported. But this method also requires extreme low temperature. A specific example is shown in the diagram below.

[Formula 6]

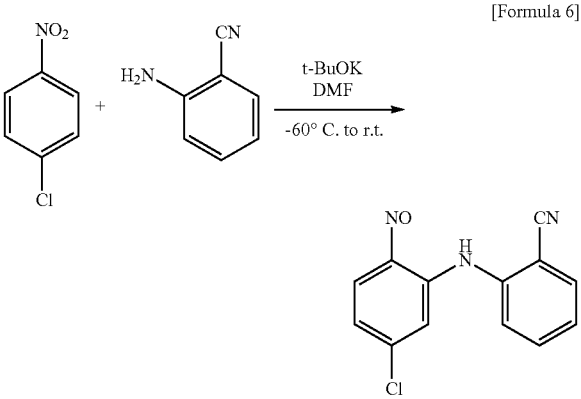

As described above, the reaction conditions of the related art include extreme low temperature. Therefore, special production facilities are required, and thus these methods are not industrially preferred. Accordingly, a production method that does not require extreme low temperature has been desired.

CITATION LIST

Patent Literature

[Patent Literature 1] WO2009/016841
[Patent Literature 2] WO2013/089002
[Patent Literature 3] Japanese Patent Laid-Open No. 2018-70520

Non Patent Literature

[Non Patent Literature 1] Synlett (2015), 1352-1356
[Non Patent Literature 2] Tetrahedron (2016), 8252-8260
[Non Patent Literature 3] Chemistry of Heterocyclic Compounds 2018, 54(9), 875-886

SUMMARY OF THE INVENTION

It is an object of the present invention to provide methods for producing a nitroso compound of a formula (3) and a quinoxaline compound of a formula (5), the method being industrially preferred, economical, and also environmentally friendly.

It is a specific object of the present invention to provide industrially preferred methods for producing a compound of a formula (3) and a compound of a formula (5) that can solve one or more disadvantages or problems in the conventional art described above.

In view of the circumstances as described above, the present inventors have diligently studied methods for producing a compound of a formula (3) and a compound of a formula (5). As a result, it has been unexpectedly found that the problem can be solved by providing the following methods for producing a compound of a formula (3) and a compound of a formula (5). Based on this finding, the present inventors have completed the present invention.

Specifically, the present invention is as follows.

[I-1] A method for producing a compound of a formula (3), comprising reacting a compound of a formula (1) with a compound of a formula (2) by using a tertiary alcohol and a base:

[Formula 7]

$$\underset{(1)}{\overset{NO_2}{\underset{R^3}{\overset{R^1}{\bigsqcup}}}\underset{R^4}{\overset{}{\bigsqcup}}} + \underset{(2)}{\overset{H_2N}{\underset{R^6}{\overset{R^9}{\bigsqcup}}}\underset{R^7}{\overset{R^8}{\bigsqcup}}} \xrightarrow{\text{Tertiary alcohol}}_{\text{Base}}$$

$$\underset{(3)}{\overset{NO}{\underset{R^3}{\overset{R^1}{\bigsqcup}}}\underset{R^4}{\overset{H}{\underset{R^5}{\overset{N}{\bigsqcup}}}\underset{R^6}{\overset{R^9}{\bigsqcup}}\underset{R^7}{\overset{R^8}{\bigsqcup}}}}$$

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy.

[I-2] The method according to [I-1], wherein the reaction of the compound of the formula (1) with the compound of the formula (2) is performed after the tertiary alcohol and the base are each added.

[I-3] The method according to [I-1] or [I-2], wherein an amount of the base used is larger than an amount of the tertiary alcohol used, in terms of equivalents.

[I-4] The method according to anyone of [I-1] to [I-3], wherein the base is one compound selected from alkali metal hydrides and alkali metal amides, or a plurality of compounds comprising a lithium-containing base as a first compound, and another compound selected from alkali metal hydrides, alkali metal amides, alkoxides, alkyl metals, alkali metals, and organic bases.

[I-5] The method according to anyone of [I-1] to [I-3], wherein the base is one compound selected from alkali metal hydrides and alkali metal amides, or a plurality of compounds comprising a lithium-containing base as a first compound, and another compound selected from alkali metal hydrides, alkali metal amides, and alkoxides.

[I-6] The method according to anyone of [I-1] to [I-3], wherein the base is sodium hydride, lithium amide, two of lithium amide and sodium hydride, two of lithium amide and sodium amide, or two of lithium amide and sodium tert-butoxide.

[I-7] The method according to any one of [I-4] to [I-6], wherein the amount of the base used is 2.0 equivalents to 4.0 equivalents per 1 equivalent of the compound of the formula (2).

[I-8] The method according to any one of [I-4] to [I-6], wherein the amount of the base used is 2.5 equivalents to 3.5 equivalents per 1 equivalent of the compound of the formula (2).

[I-9] The method according to any one of [I-4] to [I-6], wherein the amount of the base used is 2.8 equivalents to 3.5 equivalents per 1 equivalent of the compound of the formula (2).

[I-10] The method according to any one of [I-4] to [I-9], wherein the amount of the tertiary alcohol used is 0.3 equivalents to 4.0 equivalents per 1 equivalent of the compound of the formula (2).

[I-11] The method according to any one of [I-4] to [I-9], wherein the amount of the tertiary alcohol used is 0.5 equivalents to 2.0 equivalents per 1 equivalent of the compound of the formula (2).

[I-12] The method according to any one of [I-4] to [I-9], wherein the amount of the tertiary alcohol used is 0.5 equivalents to 1.5 equivalents per 1 equivalent of the compound of the formula (2).

[I-13] The method according to any one of [I-4] to [I-12], wherein the reaction is performed at −5° C. to 80° C. (preferably −5° C. to 50° C.).

[I-14] The method according to any one of [I-4] to [I-12], wherein the reaction is performed at −5° C. to 50° C.

[I-15] The method according to any one of [I-4] to [I-12], wherein the reaction is performed at 0° C. to 50° C.

[I-16] The method according to any one of [I-4] to [I-12], wherein the reaction is performed at 0° C. to 40° C.

[I-17] The method according to any one of [I-1] to [I-3], wherein the base is an alkali metal hydride.

[I-18] The method according to any one of [I-1] to [I-3], wherein the base is sodium hydride.

[I-19] The method according to [I-17] or [I-18], wherein the amount of the base used is 2.0 equivalents to 4.0 equivalents per 1 equivalent of the compound of the formula (2).

[I-20] The method according to [I-17] or [I-18], wherein the amount of the base used is 2.5 equivalents to 3.5 equivalents per 1 equivalent of the compound of the formula (2).
[I-21] The method according to [I-17] or [I-18], wherein the amount of the base used is 2.8 equivalents to 3.5 equivalents per 1 equivalent of the compound of the formula (2).
[I-22] The method according to any one of [I-17] to [I-21], wherein the amount of the tertiary alcohol used is 0.3 equivalents to 4.0 equivalents per 1 equivalent of the compound of the formula (2).
[I-23] The method according to any one of [I-17] to [I-21], wherein the amount of the tertiary alcohol used is 0.5 equivalents to 2.0 equivalents per 1 equivalent of the compound of the formula (2).
[I-24] The method according to any one of [I-17] to [I-21], wherein the amount of the tertiary alcohol used is 0.5 equivalents to 1.5 equivalents per 1 equivalent of the compound of the formula (2).
[I-25] The method according to any one of [I-17] to [I-21], wherein the amount of the tertiary alcohol used is 0.9 equivalents to 2.1 equivalents per 1 equivalent of the compound of the formula (2).
[I-26] The method according to any one of [I-17] to [I-25], wherein the reaction is performed at −5° C. to 80° C. (preferably −5° C. to 50° C.).
[I-27] The method according to any one of [I-17] to [I-25], wherein the reaction is performed at 0° C. to 50° C.
[I-28] The method according to any one of [I-17] to [I-25], wherein the reaction is performed at 20° C. to 70° C.
[I-29] The method according to any one of [I-17] to [I-25], wherein the reaction is performed at 20° C. to 40° C.
[I-30] The method according to any one of [I-1] to [I-3], wherein the base is an alkali metal amide.
[I-31] The method according to any one of [I-1] to [I-3], wherein the base is lithium amide.
[I-32] The method according to [I-30] or [I-31], wherein the amount of the base used is 2.0 equivalents to 4.0 equivalents per 1 equivalent of the compound of the formula (2).
[I-33] The method according to [I-30] or [I-31], wherein the amount of the base used is 2.5 equivalents to 3.5 equivalents per 1 equivalent of the compound of the formula (2).
[I-34] The method according to [I-30] or [I-31], wherein the amount of the base used is 2.8 equivalents to 3.5 equivalents per 1 equivalent of the compound of the formula (2).
[I-35] The method according to any one of [I-30] to [I-34], wherein the amount of the tertiary alcohol used is 0.3 equivalents to 4.0 equivalents per 1 equivalent of the compound of the formula (2).
[I-36] The method according to any one of [I-30] to [I-34], wherein the amount of the tertiary alcohol used is 0.3 equivalents to 2.5 equivalents per 1 equivalent of the compound of the formula (2).
[I-37] The method according to any one of [I-30] to [I-34], wherein the amount of the tertiary alcohol used is 0.5 equivalents to 2.0 equivalents per 1 equivalent of the compound of the formula (2).
[I-38] The method according to any one of [I-30] to [I-34], wherein the amount of the tertiary alcohol used is 0.5 equivalents to 1.5 equivalents per 1 equivalent of the compound of the formula (2).
[I-39] The method according to any one of [I-30] to [I-34], wherein the amount of the tertiary alcohol used is 0.4 equivalents to 1.1 equivalents per 1 equivalent of the compound of the formula (2).
[I-40] The method according to any one of [I-30] to [I-39], wherein the reaction is performed at −5° C. to 80° C. (preferably −5° C. to 50° C., more preferably −5° C. to 15° C.).
[I-41] The method according to any one of [I-30] to [I-39], wherein the reaction is performed at 0° C. to 50° C.
[I-42] The method according to any one of [I-30] to [I-39], wherein the reaction is performed at 0° C. to 30° C.
[I-43] The method according to any one of [I-30] to [I-39], wherein the reaction is performed at 0° C. to 15° C.
[I-44] The method according to any one of [I-1] to [I-3], wherein the base comprises a plurality of compounds.
[I-45] The method according to any one of [I-1] to [I-3], wherein the base comprises two or three compounds.
[I-46] The method according to any one of [I-1] to [I-3], wherein the base consists of two compounds.
[I-47] The method according to [I-44], wherein the plurality of compounds comprise a lithium-containing base (preferably lithium amide) as a first compound, and another compound selected from alkali metal hydrides, alkali metal amides, alkoxides, alkyl metals, alkali metals, and organic bases.
[I-48] The method according to [I-45], wherein the two or three compounds comprise a lithium-containing base (preferably lithium amide) as a first compound, and one or two other compounds selected from alkali metal hydrides, alkali metal amides, alkoxides, alkyl metals, alkali metals, and organic bases.
[I-49] The method according to [I-46], wherein the two compounds are a lithium-containing base (preferably lithium amide) as a first compound, and another compound selected from alkali metal hydrides, alkali metal amides, alkoxides, alkyl metals, alkali metals, and organic bases.
[I-50] The method according to [I-44], wherein the plurality of compounds comprise a lithium-containing base as a first compound, and another compound selected from alkali metal hydrides, alkali metal amides, and alkoxides.
[I-51] The method according to [I-45], wherein the two or three compounds comprise a lithium-containing base as a first compound, and one or two other compounds selected from alkali metal hydrides, alkali metal amides, and alkoxides.
[I-52] The method according to [I-46], wherein the two compounds are a lithium-containing base as a first compound, and another compound selected from alkali metal hydrides, alkali metal amides, and alkoxides.
[I-53] The method according to [I-44], wherein the plurality of compounds comprise lithium amide as a first compound, and another compound selected from alkali metal hydrides, alkali metal amides, and alkoxides.
[I-54] The method according to [I-45], wherein the two or three compounds comprise lithium amide as a first compound, and one or two other compounds selected from alkali metal hydrides, alkali metal amides, and alkoxides.
[I-55] The method according to [I-46], wherein the two compounds are lithium amide as a first compound, and another compound selected from alkali metal hydrides, alkali metal amides, and alkoxides.
[I-56] The method according to [I-44], wherein the plurality of compounds comprise two of lithium amide and sodium hydride, two of lithium amide and sodium amide, or two of lithium amide and sodium tert-butoxide.
[I-57] The method according to [I-45], wherein the two or three compounds comprise two of lithium amide and sodium hydride, two of lithium amide and sodium amide, or two of lithium amide and sodium tert-butoxide.

[I-58] The method according to [I-46], wherein the two compounds are two of lithium amide and sodium hydride, two of lithium amide and sodium amide, or two of lithium amide and sodium tert-butoxide.

[I-59] The method according to [I-44], wherein the plurality of compounds comprise two of lithium amide and sodium hydride.

[I-60] The method according to [I-45], wherein the two or three compounds comprise two of lithium amide and sodium hydride.

[I-61] The method according to [I-46], wherein the two compounds are lithium amide and sodium hydride.

[I-62] The method according to any one of [I-44] to [I-61], wherein the amount of the base used is 2.0 equivalents to 4.0 equivalents per 1 equivalent of the compound of the formula (2).

[I-63] The method according to any one of [I-44] to [I-61], wherein the amount of the base used is 2.5 equivalents to 3.5 equivalents per 1 equivalent of the compound of the formula (2).

[I-64] The method according to any one of [I-44] to [I-61], wherein the amount of the base used is 2.8 equivalents to 3.5 equivalents per 1 equivalent of the compound of the formula (2).

[I-65] The method according to any one of [I-44] to [I-64], wherein the amount of the tertiary alcohol used is 0.3 equivalents to 4.0 equivalents per 1 equivalent of the compound of the formula (2).

[I-66] The method according to any one of [I-44] to [I-64], wherein the amount of the tertiary alcohol used is 0.3 equivalents to 2.5 equivalents per 1 equivalent of the compound of the formula (2).

[I-67] The method according to any one of [I-44] to [I-64], wherein the amount of the tertiary alcohol used is 0.5 equivalents to 2.5 equivalents per 1 equivalent of the compound of the formula (2).

[I-68] The method according to any one of [I-44] to [I-64], wherein the amount of the tertiary alcohol used is 0.5 equivalents to 2.0 equivalents per 1 equivalent of the compound of the formula (2).

[I-69] The method according to any one of [I-44] to [I-64], wherein the amount of the tertiary alcohol used is 0.5 equivalents to 1.5 equivalents per 1 equivalent of the compound of the formula (2).

[I-70] The method according to any one of [I-47] to [I-69], wherein a ratio of another compound is more than 0 equivalents and 2.0 equivalents or less per 1 equivalent of the first compound.

[I-71] The method according to any one of [I-47] to [I-69], wherein a ratio of another compound is more than 0 (zero) equivalents and 0.5 equivalents or less per 1 equivalent of the first compound.

[I-72] The method according to any one of [I-47] to [I-69], wherein a ratio of another compound is 0.2 equivalents to 0.5 equivalents per 1 equivalent of the first compound.

[I-73] The method according to any one of [I-44] to [I-72], wherein the reaction is performed at −5° C. to 80° C. (preferably −5° C. to 50° C.).

[I-74] The method according to any one of [I-44] to [I-72], wherein the reaction is performed at 0° C. to 60° C.

[I-75] The method according to any one of [I-44] to [I-72], wherein the reaction is performed at 0° C. to 50° C.

[I-76] The method according to any one of [I-44] to [I-72], wherein the reaction is performed at 0° C. to 30° C.

[I-77] The method according to any one of [I-1] to [I-76], wherein the tertiary alcohol is a compound of a formula (6):

[Formula 8]

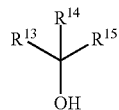

(6)

wherein $R^{13}$, $R^{14}$, and $R^{15}$ may be the same or different and are each a (C1-C6) alkyl, a (C3-C6) cycloalkyl, a (C2-C6) alkenyl, a (C2-C6) alkynyl, a (C6-C10) aryl, or a (C6-C10) aryl (C1-C4) alkyl, and two selected from $R^{13}$, $R^{14}$, and $R^{15}$ may be bonded to each other to form a ring.

[I-78] The method according to [I-77], wherein $R^{13}$, $R^{14}$, and $R^{15}$ may be the same or different and is selected from methyl, ethyl, ethenyl, ethynyl, propyl, benzyl, and phenyl.

[I-79] The method according to any one of [I-1] to [I-76], wherein the tertiary alcohol is selected from tert-butanol, 2-methyl-2-butanol, 2-methyl-3-buten-2-ol, and 2-methyl-1-phenyl-2-propanol.

[I-80] The method according to any one of [I-1] to [I-76], wherein the tertiary alcohol is tert-butanol.

[I-81] The method according to any one of [I-1] to [I-80], wherein the reaction is performed in the presence of a solvent.

[I-82] The method according to [I-81], wherein the reaction of the compound of the formula (1) with the compound of the formula (2) is performed after the tertiary alcohol and the base are each added to the solvent.

[I-83] The method according to [I-81] or [I-82], wherein the solvent is toluene, xylene, chlorobenzene, dichlorobenzene, or a mixture thereof.

[I-84] The method according to [I-81] or [I-82], wherein the solvent is toluene, xylene, or a mixture thereof.

[I-85] The method according to [I-81] or [I-82], wherein the solvent is toluene.

[I-86] The method according to any one of [I-1] to [I-85], wherein
$R^1$, $R^2$, $R^3$, and $R^4$ are each independently a hydrogen atom, a fluorine atom, or a chlorine atom; and
$R^5$, $R^6$, $R^7$, $R^8$, and $R^9$ are each independently a hydrogen atom, a (C1-C4) alkyl, or a (C1-C4) alkoxy.

[I-87] The method according to any one of [I-1] to [I-85], wherein
$R^1$, $R^2$, $R^3$, and $R^4$ are each independently a hydrogen atom or a chlorine atom; and
$R^5$, $R^6$, $R^7$, $R^8$, and $R^9$ are each independently a hydrogen atom or a (C1-C4) alkoxy.

[I-88] The method according to any one of [I-1] to [I-85], wherein
$R^1$ is a hydrogen atom or a chlorine atom;
$R^2$, $R^3$, and $R^4$ are each a hydrogen atom;
$R^5$, $R^6$, $R^8$, and $R^9$ are each a hydrogen atom; and
$R^7$ is a hydrogen atom or methoxy.

[I-89] The method according to any one of [I-1] to [I-85], wherein
$R^1$ is a hydrogen atom or a chlorine atom;
$R^2$, $R^3$, and $R^4$ are each a hydrogen atom;
$R^5$, $R^6$, $R^8$, and $R^9$ are each a hydrogen atom; and
$R^7$ is methoxy.

[I-90] The method according to any one of [I-1] to [I-85], wherein
$R^1$ is a chlorine atom;
$R^2$, $R^3$, and $R^4$ are each a hydrogen atom;
$R^5$, $R^6$, $R^8$, and $R^9$ are each a hydrogen atom; and
$R^7$ is methoxy.

[II-1] A method for producing a compound of a formula (5), formula (5):

[Formula 9]

(5)

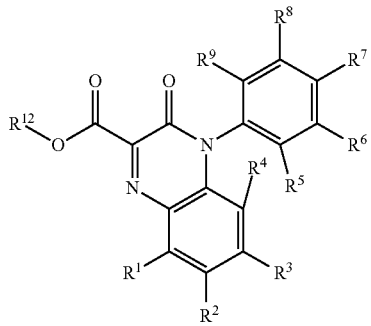

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy; and
$R^{12}$ is a hydrogen atom, an alkali metal atom, or a (C1-C4) alkyl, the method comprising the following steps;
step (i) reacting a compound of a formula (1) with a compound of a formula (2) by using a tertiary alcohol and a base, to obtain a compound of a formula (3):

[Formula 10]

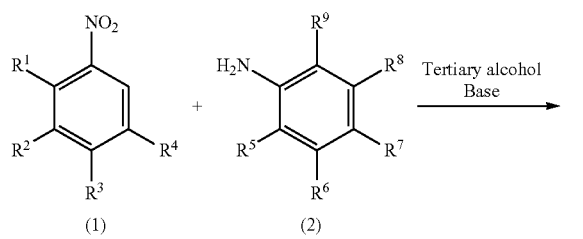

wherein $R^1$, $R^2$, $R^3$, $R^4$, $R^5$, $R^6$, $R^7$, $R^8$, and $R^9$ are as defined above, and wherein the step (i) is performed by the method according to any one of [I-1] to [I-90], step (ii) reacting the compound of the formula (3) with a compound of a formula (4) to obtain the compound of the formula (5):

[Formula 11]

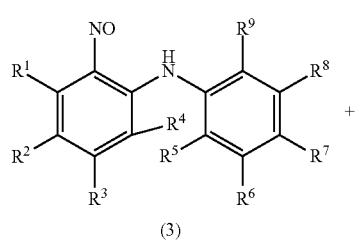

(3)

-continued

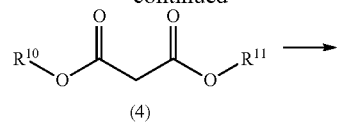

(4)

(5)

wherein $R^1$, $R^2$, $R^3$, $R^4$, $R^5$, $R^6$, $R^7$, $R^8$, and $R^9$ are as defined above;
$R^{10}$ and $R^{11}$ are each independently a (C1-C4) alkyl; and
$R^{12}$ is as defined above.

[II-2] A method for producing a compound of a formula (5):

[Formula 12]

(5)

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy; and
$R^{12}$ is a hydrogen atom, an alkali metal atom, or a (C1-C4) alkyl, the method comprising using a compound of a formula (3):

[Formula 13]

(3)

wherein $R^1$, $R^2$, $R^3$, $R^4$, $R^5$, $R^6$, $R^7$, $R^8$, and $R^9$ are as defined above,
wherein the compound of the formula (3) is produced by the method according to any one of [I-1] to [I-90].

[II-3] A method for producing a compound of a formula (5):

[Formula 14]

(5)

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy; and
$R^{12}$ is a hydrogen atom, an alkali metal atom, or a (C1-C4) alkyl, the method comprising using a compound of a formula (3):

[Formula 15]

(3)

wherein $R^1$, $R^2$, $R^3$, $R^4$, $R^5$, $R^6$, $R^7$, $R^8$, and $R^9$ are as defined above, wherein as the compound of the formula (3), the compound of the formula (3) produced by the method according to any one of [I-1] to [I-90] is used.

[II-4] A method for producing a compound of a formula (5), formula (5):

[Formula 16]

(5)

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy; and $R^{12}$ is a hydrogen atom, an alkali metal atom, or a (C1-C4) alkyl,
the method comprising the following steps;
step (i) obtaining a compound of a formula (3) by the method according to any one of [I-1] to [I-90]:

[Formula 17]

(3)

wherein $R^1$, $R^2$, $R^3$, $R^4$, $R^5$, $R^6$, $R^7$, $R^8$, and $R^9$ are as defined above,
step (ii) reacting the compound of the formula (3) with a compound of a formula (4) to obtain the compound of the formula (5):

[Formula 18]

(3)

(4)

(5)

wherein $R^1$, $R^2$, $R^3$, $R^4$, $R^5$, $R^6$, $R^7$, $R^8$, $R^9$, $R^{10}$, $R^{11}$, and $R^{12}$ are as defined above.

[II-5] The method according to [II-1] or [II-4], wherein the compound of the formula (4) is dimethyl malonate or diethyl malonate.

[II-6] The method according to [II-1] or [II-4], wherein the reaction in the step (ii) is performed at pH 8 or more.

[II-7] The method according to [II-1] or [II-4], wherein the reaction in step (ii) is performed at pH 8 to 14.

[II-8] The method according to any one of [II-1], [II-4] to [II-7], wherein the reaction in step (ii) is performed in the absence of a phase transfer catalyst.

[II-9] The method according to any one of [II-1], [II-4] to [II-7], wherein the reaction in step (ii) is performed in the presence of a phase transfer catalyst.

[II-10] The method according to any one of [II-1], [II-4] to [II-9], wherein the reaction in step (ii) is performed in the presence of water.

[II-11] The method according to any one of [II-1] to [II-10], wherein
$R^1$, $R^2$, $R^3$, and $R^4$ are each independently a hydrogen atom, a fluorine atom, or a chlorine atom; and
$R^5$, $R^6$, $R^7$, $R^8$, and $R^9$ are each independently a hydrogen atom, a (C1-C4) alkyl, or a (C1-C4) alkoxy.

[II-12] The method according to any one of [II-1] to [II-10], wherein
$R^1$, $R^2$, $R^3$, and $R^4$ are each independently a hydrogen atom or a chlorine atom; and
$R^5$, $R^6$, $R^7$, $R^8$, and $R^9$ are each independently a hydrogen atom or a (C1-C4) alkoxy.

[II-13] The method according to any one of [II-1] to [II-10], wherein
$R^1$ is a hydrogen atom or a chlorine atom;
$R^2$, $R^3$, and $R^4$ are each a hydrogen atom;
$R^5$, $R^6$, $R^8$, and $R^9$ are each a hydrogen atom; and
$R^7$ is a hydrogen atom or methoxy.

[II-14] The method according to any one of [II-1] to [II-10], wherein
$R^1$ is a hydrogen atom or a chlorine atom;
$R^2$, $R^3$, and $R^4$ are each a hydrogen atom;
$R^5$, $R^6$, $R^8$, and $R^9$ are each a hydrogen atom; and
$R^7$ is methoxy.

[II-15] The method according to any one of [II-1] to [II-10], wherein
$R^1$ is a chlorine atom;
$R^2$, $R^3$, and $R^4$ are each a hydrogen atom;
$R^5$, $R^6$, $R^8$, and $R^9$ are each a hydrogen atom; and
$R^7$ is methoxy.

[II-16] The method according to any one of [II-1] to [II-15], wherein
$R^{10}$ and $R^{11}$ are each methyl or ethyl; and
$R^{12}$ is a hydrogen atom, a lithium atom, a sodium atom, a potassium atom, methyl, or ethyl.

[II-17] The method according to any one of [II-1] to [II-15], wherein
$R^{10}$ and $R^{11}$ are each methyl or ethyl; and
$R^{12}$ is a hydrogen atom, a lithium atom, a sodium atom, methyl, or ethyl.

[II-18] The method according to any one of [II-1] to [II-15], wherein
$R^{10}$ and $R^{11}$ are each methyl or ethyl; and
$R^{12}$ is a hydrogen atom, a lithium atom, or a sodium atom.

[II-19] The method according to any one of [II-1] to [II-15], wherein
$R^{10}$ and $R^{11}$ are each methyl or ethyl; and
$R^{12}$ is a hydrogen atom.

[III-1] A method for producing a compound of a formula (3), comprising reacting a compound of a formula (1) with a compound of a formula (2) by using a tertiary alcohol and a base:

[Formula 19]

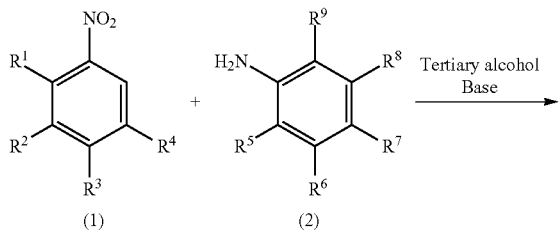

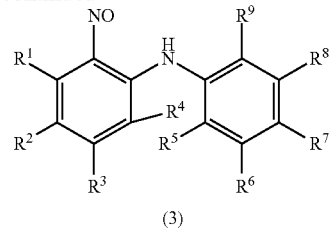

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy.

[III-2] The method according to [III-1], wherein the reaction of the compound of the formula (1) with the compound of the formula (2) is performed after the tertiary alcohol and the base are each added.

[III-3] The method according to [III-1] or [III-2], wherein an amount of the base used is larger than an amount of the tertiary alcohol used, in terms of equivalents.

[III-4] The method according to any one of [III-1] to [III-3], wherein the base is one compound selected from alkali metal hydrides and alkali metal amides, or a plurality of compounds comprising a lithium-containing base as a first compound, and a second compound selected from alkali metal hydrides, alkali metal amides, alkoxides, alkyl metals, alkali metals, and organic bases.

[III-5] The method according to any one of [III-1] to [III-3], wherein the base is sodium hydride, lithium amide, two of lithium amide and sodium hydride, two of lithium amide and sodium amide, or two of lithium amide and sodium tert-butoxide.

[III-6] The method according to [III-4] or [III-5], wherein the amount of the base used is 2.0 equivalents to 4.0 equivalents per 1 equivalent of the compound of the formula (2), and the amount of the tertiary alcohol used is 0.3 equivalents to 4.0 equivalents per 1 equivalent of the compound of the formula (2).

[III-7] The method according to any one of [III-1] to [III-3], wherein the base is an alkali metal hydride.

[III-8] The method according to any one of [III-1] to [III-3], wherein the base is sodium hydride.

[III-9] The method according to [III-7] or [III-8], wherein the amount of the base used is 2.0 equivalents to 4.0 equivalents per 1 equivalent of the compound of the formula (2), and the amount of the tertiary alcohol used is 0.3 equivalents to 4.0 equivalents per 1 equivalent of the compound of the formula (2).

[III-10] The method according to anyone of [III-1] to [III-3], wherein the base is an alkali metal amide.

[III-11] The method according to anyone of [III-1] to [III-3], wherein the base is lithium amide.

[III-12] The method according to [III-10] or [III-11], wherein the amount of the base used is 2.0 equivalents to 4.0 equivalents per 1 equivalent of the compound of the formula (2), and the amount of the tertiary alcohol used is 0.3 equivalents to 2.5 equivalents per 1 equivalent of the compound of the formula (2).

[III-13] The method according to anyone of [III-1] to [III-3], wherein the base comprises a plurality of compounds.

[III-14] The method according to [III-13], wherein the plurality of compounds comprise a lithium-containing base as a first compound, and a second compound selected from alkali metal hydrides, alkali metal amides, alkoxides, alkyl metals, alkali metals, and organic bases.

[III-15] The method according to [III-13], wherein the plurality of compounds comprise two of lithium amide and sodium hydride, two of lithium amide and sodium amide, or two of lithium amide and sodium tert-butoxide.

[III-16] The method according to [III-13], wherein the plurality of compounds comprise two of lithium amide and sodium hydride.

[III-17] The method according to anyone of [III-13] to [III-16], wherein the amount of the base used is 2.0 equivalents to 4.0 equivalents per 1 equivalent of the compound of the formula (2), and the amount of the tertiary alcohol used is 0.3 equivalents to 2.5 equivalents per 1 equivalent of the compound of the formula (2).

[III-18] The method according to any one of [III-1] to [III-17], wherein the tertiary alcohol is a compound of a formula (6):

[Formula 20]

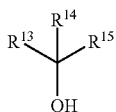

(6)

wherein $R^{13}$, $R^{14}$, and $R^{15}$ may be the same or different and are each a (C1-C6) alkyl, a (C3-C6) cycloalkyl, a (C2-C6) alkenyl, a (C2-C6) alkynyl, a (C6-C10) aryl, or a (C6-C10) aryl (C1-C4) alkyl, and two selected from $R^{13}$, $R^{14}$, and $R^{15}$ may be bonded to each other to form a ring.

[III-19] The method according to any one of [III-1] to [III-17], wherein the tertiary alcohol is selected from tert-butanol, 2-methyl-2-butanol, 2-methyl-3-buten-2-ol, and 2-methyl-1-phenyl-2-propanol.

[III-20] The method according to anyone of [III-1] to [III-19], wherein the reaction is performed at −5° C. to 80° C.

[III-21] The method according to anyone of [III-1] to [III-19], wherein the reaction is performed at 0° C. to 50° C.

[III-22] The method according to anyone of [III-1] to [III-21], wherein $R^1$ is a hydrogen atom or a chlorine atom;

$R^2$, $R^3$, and $R^4$ are each a hydrogen atom;

$R^5$, $R^6$, $R^8$, and $R^9$ are each a hydrogen atom; and $R^7$ is a hydrogen atom or methoxy.

[III-23] The method according to anyone of [III-1] to [III-21], wherein $R^1$ is a chlorine atom;

$R^2$, $R^3$, and $R^4$ are each a hydrogen atom;

$R^5$, $R^6$, $R^8$, and $R^9$ are each a hydrogen atom; and $R^7$ is methoxy.

[III-24] A method for producing a compound of a formula (5), formula (5):

[Formula 21]

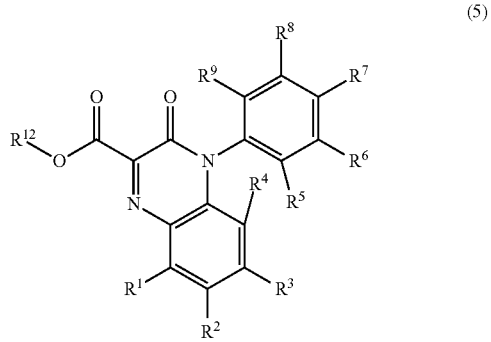

(5)

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy; and $R^{12}$ is a hydrogen atom, an alkali metal atom, or a (C1-C4) alkyl, the method comprising the following steps;

step (i) obtaining a compound of a formula (3) by the method according to any one of [III-1] to [III-23]:

[Formula 22]

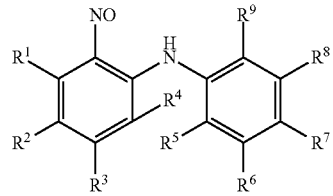

(3)

wherein $R^1$, $R^2$, $R^3$, $R^4$, $R^5$, $R^6$, $R^7$, $R^8$, and $R^9$ are as defined above, step (ii) reacting the compound of the formula (3) with a compound of a formula (4) to obtain the compound of the formula (5):

[Formula 23]

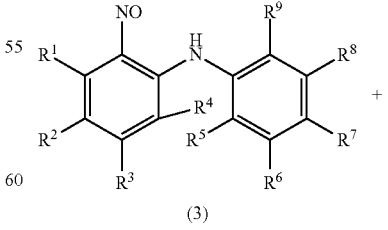

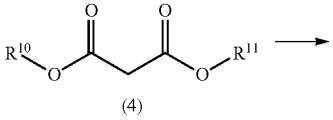

(4)

-continued

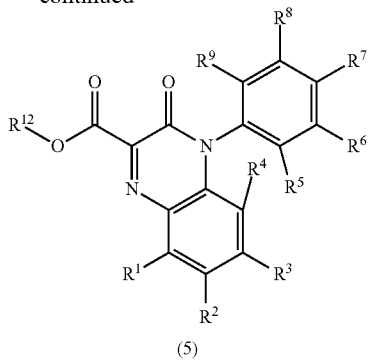

(5)

wherein $R^1$, $R^2$, $R^3$, $R^4$, $R^5$, $R^6$, $R^7$, $R^8$, $R^9$, $R^{10}$, $R^{11}$, and $R^{12}$ are as defined above.

[III-25] The method according to [III-24], wherein the reaction in step (ii) is performed at pH 8 or more.

[III-26] The method according to [III-24], wherein the reaction in step (ii) is performed at pH 8 to 14.

[III-27] The method according to any one of [III-24] to [III-26], wherein the reaction in step (ii) is performed in the absence of a phase transfer catalyst.

[III-28] The method according to any one of [III-24] to [III-26], wherein the reaction in step (ii) is performed in the presence of a phase transfer catalyst.

[III-29] The method according to any one of [III-24] to [III-28], wherein the reaction in step (ii) is performed in the presence of water.

[III-30] The method according to any one of [III-24] to [III-29], wherein
$R^{10}$ and $R^{11}$ are each methyl or ethyl; and
$R^{12}$ is a hydrogen atom, a lithium atom, a sodium atom, a potassium atom, methyl, or ethyl.

[III-31] The method according to anyone of [III-24] to [III-29], wherein
$R^{10}$ and $R^{11}$ are each methyl or ethyl; and
$R^{12}$ is a hydrogen atom.

Advantageous Effects of Invention

According to the present invention, novel methods for producing a compound of a formula (3) and a compound of a formula (5) are provided, the methods being industrially preferred, economical, and also environmentally friendly. According to the present invention, methods for producing a compound of a formula (3) and a compound of a formula (5) that can solve one or more disadvantages or problems in the conventional art described above are provided.

DESCRIPTION OF EMBODIMENTS

The present invention will be described in detail below.
Herein, the following abbreviations and prefixes may be used, and their meanings are as follows:
Me: methyl
Et: ethyl
Pr, n-Pr, and Pr-n: propyl (that is, normal propyl)
i-Pr and Pr-i: isopropyl
Bu, n-Bu, and Bu-n: butyl (that is, normal butyl)
s-Bu and Bu-s: sec-butyl (that is, secondary butyl)
i-Bu and Bu-i: isobutyl
t-Bu and Bu-t: tert-butyl (that is, tertiary butyl)
Ph: phenyl
n—: normal
s- and sec-: secondary
i- and iso-: iso
t- and tert-: tertiary
neo-: neo
c- and cyc-: cyclo
o—: ortho
m—: meta
p—: para
t-BuOH: tert-butanol Examples of a halogen atom include a fluorine atom, a chlorine atom, a bromine atom, and an iodine atom.

As used herein, general terms such as "alkyl" are construed to include both straight chains and branched chains such as butyl and tert-butyl. On the other hand, for example, the specific term "butyl" means straight chain "normal butyl" and does not mean branched chain "tert-butyl". Branched chain isomers such as "tert-butyl" are specifically mentioned when intended.

(Ca-Cb) means that the number of carbon atoms is a to b. For example, the "(C1-C4)" of a "(C1-C4) alkyl" means that the number of carbon atoms of the alkyl is 1 to 4.

A (C1-C6) alkyl means a straight chain or branched chain alkyl having 1 to 6 carbon atoms. Examples of the (C1-C6) alkyl include, but are not limited to, methyl, ethyl, propyl, isopropyl, butyl, sec-butyl, isobutyl, tert-butyl, pentyl, and hexyl.

A (C1-C4) alkyl means a straight chain or branched chain alkyl having 1 to 4 carbon atoms. Examples of the (C1-C4) alkyl are methyl, ethyl, propyl, isopropyl, butyl, sec-butyl, isobutyl, and tert-butyl.

A (C3-C6) cycloalkyl means a cycloalkyl having 3 to 6 carbon atoms. Examples of the (C3-C6) cycloalkyl are cyclopropyl, cyclobutyl, cyclopentyl, and cyclohexyl.

A (C2-C6) alkenyl means a straight chain or branched chain alkenyl having 2 to 6 carbon atoms. Examples of the (C2-C6) alkenyl include, but are not limited to, vinyl (that is, ethenyl), 1-propenyl, isopropenyl, 2-propenyl, 1-butenyl, 1-methyl-1-propenyl, 2-methyl-1-propenyl, 2-butenyl, 3-butenyl, 1,3-butadienyl, 1-pentenyl, and 1-hexenyl.

A (C2-C6) alkynyl means a straight chain or branched chain alkynyl having 2 to 6 carbon atoms. Examples of the (C2-C6) alkynyl include, but are not limited to, ethynyl, 1-propynyl, 2-propynyl, 1-butynyl, 1-methyl-2-propynyl, 2-butynyl, 3-butynyl, 1-pentynyl, and 1-hexynyl.

Examples of a (C6-C10) aryl are phenyl, 1-naphthyl, and 2-naphthyl.

A (C6-C10) aryl (C1-C4) alkyl means a (C1 to C4 alkyl) substituted by a (C6 to C10) aryl (here, the C6 to C10 aryl moiety and the C1 to C4 alkyl moiety have the same meanings as the above definitions). Examples of the (C6-C10) aryl (C1-C4) alkyl include, but are not limited to, benzyl, 1-phenylethyl, 2-phenylethyl, 3-phenylpropyl, 4-phenylbutyl, naphthalen-1-ylmethyl, and a naphthalen-2-ylmethyl group.

A (C1-C4) alkoxy means (C1-C4) alkyl-O— (here, the (C1-C4) alkyl moiety has the same meaning as the above definition). Examples of the (C1-C4) alkoxy include methoxy, ethoxy, propoxy, isopropoxy, butoxy, sec-butoxy, isobutoxy, and tert-butoxy.

Examples of the "ring" in the expression "two may be bonded to each other to form a ring" include, but are not limited to, cyclopropane, cyclobutane, cyclopentane, cyclohexane, cyclopentene, and cyclohexene. The "ring" may be condensed with another "ring".

As used herein, the non-limiting terms "comprise(s)/comprising" can each be optionally replaced by the limiting expressions "consist(s) of/consisting of."

As used herein, the expression "after . . . are each added" can be replaced by the expression "after . . . are separately added."

As seen from Examples described later, the expression "the tertiary alcohol and the base are each added" can be understood to mean, for example, that "the tertiary alcohol and the base are each added to the reaction system," but this is not interpreted as a limitation. Therefore, as used herein, the expression "after the tertiary alcohol and the base are each added" can be replaced by the expression, for example, "after the tertiary alcohol and the base are each added to the reaction system."

As used herein, the expression "second compound" can be replaced by the expression "another compound"/"other compound".

The method of the present invention will be described.
(Step (i))
Step (i) will be described.
Step (i) is the step of reacting a compound of a formula (1) with a compound of a formula (2) by using a tertiary alcohol and a base, to produce a compound of a formula (3).

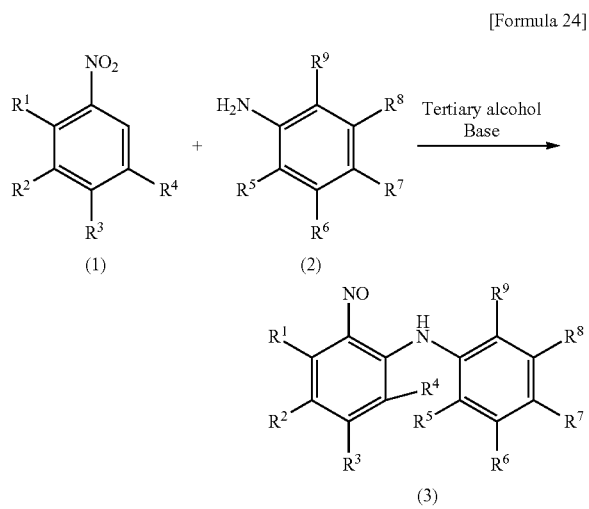

[Formula 24]

wherein $R^1$, $R^2$, $R^3$, $R^4$, $R^5$, $R^6$, $R^7$, $R^8$, and $R^9$ are as defined above.
(Raw Material: Compound of Formula (1), which is Nitro Compound)

As a raw material in step (i), the compound of the formula (1), which is a nitro compound, is used. The compound of the formula (1) is a known compound or can be produced from a known compound according to a known method.

Specific examples of the compound of the formula (1) include, but are not limited to, the following;
nitrobenzene, 2-chloronitrobenzene, 3-chloronitrobenzene, 4-chloronitrobenzene, 2-fluoronitrobenzene, 3-fluoronitrobenzene, and 4-fluoronitrobenzene.

In view of yield, availability, price, the usefulness of the product, and the like, preferred specific examples of the compound of the formula (1) include nitrobenzene and 2-chloronitrobenzene, more preferably 2-chloronitrobenzene.

The amount of the compound of the formula (1) used may be an arbitrary amount as long as the reaction proceeds. However, in one aspect, the amount of the compound of the formula (1) (nitro compound) used is, for example, 0.7 equivalents to 2.0 equivalents, preferably 0.9 equivalents to 1.8 equivalents, more preferably 0.9 equivalents to 1.6 equivalents, further preferably 0.9 equivalents to 1.5 equivalents, and particularly preferably 1.0 to 1.5 equivalents per 1 equivalent of the compound of the formula (2) (aniline compound), in view of yield, by-product suppression, economic efficiency, and the like. From the same viewpoint as the above, in another aspect, the amount of the compound of the formula (1) (nitro compound) used is, for example, 1.0 equivalent to 2.0 equivalents, preferably 1.0 equivalent to 1.8 equivalents, more preferably 1.0 equivalent to 1.6 equivalents, and particularly preferably 1.0 equivalent to 1.5 equivalents per 1 equivalent of the compound of the formula (2) (aniline compound).

As used herein, the definition of "the equivalent of the compound of the formula (1) (nitro compound)" is as follows, or the term "equivalent" is construed according to the following examples. For example, "1 equivalent of the compound of the formula (1) (nitro compound) per 1 equivalent of the compound of the formula (2) (aniline compound)" means "1 mol of the compound of the formula (1) (nitro compound) per 1 mol of the compound of the formula (2) (aniline compound)." For example, "0.5 equivalents of the compound of the formula (1) (nitro compound) per 1 equivalent of the compound of the formula (2) (aniline compound)" means "0.5 mol of the compound of the formula (1) (nitro compound) per 1 mol of the compound of the formula (2) (aniline compound)."
(Raw Material: Compound of General Formula (2), which is Aniline Compound)

As a raw material in step (i), the compound of the formula (2), which is an aniline compound, is used. The compound of the formula (2) is a known compound or can be produced from a known compound according to a known method.

Specific examples of the compound of the formula (2) include, but are not limited to, the following;
aniline, 4-methoxyaniline (that is, p-anisidine), 4-ethoxyaniline, 4-n-propoxyaniline, 4-n-butoxyaniline, 4-methylaniline, 4-ethylaniline, 4-n-propylaniline, 4-n-butylaniline, and 4-t-butylaniline.

In view of yield, the usefulness of the product, and/or the like, preferred specific examples of the compound of the formula (2) include aniline or 4-methoxyaniline. In view of the usefulness of the product, and the like, a more preferred specific example of the compound of the formula (2) is 4-methoxyaniline.

In view of the improvement of the economy, the reduction of the environmental load, and the like, the use of an excessive amount of 2-chloronitrobenzene or nitrobenzene is acceptable. On the other hand, the use of an excessive amount of p-anisidine is preferably avoided, but this is not interpreted as a limitation. For example, it was clear that p-anisidine is far expensive compared with 2-chloronitrobenzene and nitrobenzene. In the method of Japanese Patent Laid-Open No. 2018-70520 (Patent Literature 3), 2 equivalents or more of p-anisidine is required as the raw material excessively used. In fact, in Examples of Japanese Patent Laid-Open No. 2018-70520 (Patent Literature 3), as much as 2 equivalents to 3 equivalents of p-anisidine is used. On the other hand, in the method of the present invention, 2 equivalents or less of 2-chloronitrobenzene or chloronitrobenzene is sufficient as the raw material excessively used. As shown in Examples described later, even 1 equivalent to 1.5 equivalents of 2-chloronitrobenzene or chloronitrobenzene provides a satisfactory yield.
(Base in Step (i))

Examples of the base in step (i) include, but are not limited to, the following; alkali metal hydrides (for example, lithium hydride, sodium hydride, and potassium hydride, preferably sodium hydride and potassium hydride, and more preferably sodium hydride), alkaline earth metal hydrides (for example, calcium hydride), alkoxides (for example, lithium tert-butoxide, sodium tert-butoxide, potassium tert-butoxide, lithium methoxide, sodium methoxide, potassium methoxide, lithium ethoxide, sodium ethoxide, potassium ethoxide, lithium isopropoxide, sodium isopropoxide, and potassium isopropoxide, preferably lithium tert-butoxide, sodium tert-butoxide, and potassium tert-butoxide, and more preferably sodium tert-butoxide), alkyl metals (for example, butyllithium, sec-butyllithium, and tert-butyllithium), alkali metal amides (for example, lithium amide, sodium amide, potassium amide, lithium diisopropylamide, and potassium hexamethyldisilazide, preferably lithium amide, sodium amide, and potassium amide, more preferably lithium amide and sodium amide, and further preferably lithium amide), alkali metals (for example, lithium metal, sodium metal, and potassium metal), organic bases (for example, trimethylamine, triethylamine, tripropylamine, tributylamine, diisopropylethylamine, 1,8-diazabicyclo[5.4.0]-7-undec-7-ene (DBU), 1,5-diazabicyclo[4.3.0]non-5-ene (DBN), 1,4-diazabicyclo[2.2.2]octane (DABCO), pyridine, N,N-dimethyl-4-aminopyridine, N,N-dimethylaniline, and N,N-diethylaniline), and any combination thereof in an arbitrary ratio.

In view of yield, by-product suppression, economic efficiency, and the like, preferred examples of the base in step (i) include alkali metal hydrides, alkali metal amides, and any combination thereof in an arbitrary ratio. Preferred specific examples of the base in step (i) include lithium hydride, sodium hydride, potassium hydride, lithium amide, sodium amide, and any combination thereof in an arbitrary ratio, more preferably lithium hydride, sodium hydride, potassium hydride, and lithium amide, and further preferably sodium hydride and lithium amide.

The base in step (i) may include a plurality of compounds. The first compound is preferably a lithium-containing base. The second compound (also referred to as another compound/other compound) can be selected from alkali metal hydrides, alkali metal amides, alkoxides, alkyl metals, alkali metals, and organic bases.

Examples of the lithium-containing base include, but are not limited to, lithium hydride, lithium amide, lithium diisopropylamide, lithium tert-butoxide, butyllithium, sec-butyllithium, tert-butyllithium, lithium metal, lithium hydroxide, lithium carbonate, and lithium hydrogen carbonate. Preferred examples of the lithium-containing base are lithium hydride, lithium amide, lithium diisopropylamide, lithium tert-butoxide, butyllithium, sec-butyllithium, tert-butyllithium, and lithium metal, more preferably lithium hydride and lithium amide, and particularly preferably lithium amide.

The first compound and the second compound can be used in an arbitrary ratio. A suitable ratio is selected according to the types of the compounds used. In one aspect, for example, the ratio of the second compound to the first compound is more than 0 (zero) equivalents and 3.0 equivalents or less, or more than 0 (zero) equivalents and 2.0 equivalents or less, preferably more than 0 (zero) equivalents and 1.5 equivalents or less, more preferably more than 0 (zero) equivalents and 1.0 equivalent or less, and further preferably more than 0 (zero) equivalents and 0.5 equivalents or less. In another aspect, for example, the ratio of the second compound to the first compound is preferably 0.05 equivalents to 1.5 equivalents, more preferably 0.1 equivalents to 1.0 equivalent, and further preferably 0.2 equivalents to 0.5 equivalents per 1 equivalent of the first compound.

A preferred specific example of the combination of the plurality of compounds is two of lithium amide and sodium hydride, two of lithium amide and sodium amide, or two of lithium amide and sodium tert-butoxide, in one aspect. Here, "plurality of" means, for example, "two or more" and is preferably "two or three" or "two," more preferably "two." In another aspect, a preferred specific example of the combination of the plurality of compounds is two of lithium amide as the first compound and sodium hydride as the second compound, two of lithium amide as the first compound and sodium amide as the second compound, or two of lithium amide as the first compound and sodium tert-butoxide as the second compound.

The form of the base in step (i) may be any form as long as the reaction proceeds. The form of the base in step (i) can be suitably selected by those skilled in the art.

The amount of the base used in step (i) may be an arbitrary amount as long as the reaction proceeds. However, in view of yield, by-product suppression, economic efficiency, and the like, when the base is an alkali metal hydride (preferably sodium hydride), the amount of the base used in step (i) is, for example, usually 2.0 equivalents or more, preferably 2.0 equivalents to 4.0 equivalents, more preferably 2.5 equivalents to 3.5 equivalents, and further preferably 2.5 equivalents to 3.1 equivalents per 1 equivalent of the compound of the formula (2) (aniline compound), in one aspect, and, for example, preferably 2.8 equivalents to 3.5 equivalents, in another aspect.

From the same viewpoint as the above, when the base is an alkali metal amide (preferably lithium amide), the amount of the base used in step (i) is, for example, usually 2.0 equivalents or more, preferably 2.0 equivalents to 4.0 equivalents, and more preferably 2.5 equivalents to 3.5 equivalents per 1 equivalent of the compound of the formula (2) (aniline compound), in one aspect, and, for example, preferably 2.8 equivalents to 3.5 equivalents, in another aspect.

When the base comprises a plurality of compounds, the amount of the base used (the total amount of the compounds used) in step (i) is, for example, usually 2.0 equivalents or more, preferably 2.0 equivalents to 4.0 equivalents, and more preferably 2.5 equivalents to 3.5 equivalents per 1 equivalent of the compound of the formula (2) (aniline compound), in one aspect, and, for example, more preferably 2.8 equivalents to 3.5 equivalents, in another aspect.

As described above, the definition of "the equivalent of the base" as used herein is as follows, or the term "equivalent" is construed according to the following examples. For example, when the base is a monovalent base such as sodium hydride (NaH) and lithium amide (LiNH$_2$), "1 equivalent of the base per 1 equivalent of the compound of the formula (2) (aniline compound)" means "1 mol of the base per 1 mol of the compound of the formula (2) (aniline compound)," and "0.5 equivalents of the base per 1 equivalent of the compound of the formula (2) (aniline compound)" means "0.5 mol of the base per 1 mol of the compound of the formula (2) (aniline compound)." As another example, when the base is a divalent base such as calcium hydride (CaH$_2$), "1 equivalent of the base per 1 equivalent of the compound of the formula (2) (aniline compound)" means "0.5 mol of the base per 1 mol of the compound of the formula (2) (aniline compound)," and "0.5 equivalents of the base per 1 equivalent of the compound of the formula (2) (aniline compound)" means "0.25 mol of the base per 1 mol of the compound of the formula (2) (aniline compound)."

A predetermined amount of the base used can be added to the reaction at once. Alternatively, the base may be added in a plurality of portions or by dropping.

(Tertiary Alcohol in Step (i))

The tertiary alcohol in step (i) includes a compound of a formula (6).

[Formula 25]

(6)

wherein $R^{13}$, $R^{14}$, and $R^{15}$ may be the same or different and are each a (C1-C6) alkyl, a (C3-C6) cycloalkyl, a (C2-C6) alkenyl, a (C2-C6) alkynyl, a (C6-C10) aryl, or a (C6-C10) aryl (C1-C4) alkyl, and two selected from $R^{13}$, $R^{14}$, and $R^{15}$ may be bonded to each other to form a ring.

Examples of the tertiary alcohol in step (i) include, but are not limited to, tert-butanol, 2-methyl-2-butanol, 2-methyl-2-pentanol, 3-methyl-3-pentanol, 3-ethyl-3-pentanol, 2-methyl-3-buten-2-ol, 2-methyl-3-butyn-2-ol, 1-methylcyclopentanol, 1-ethylcyclopentanol, 1-propylcyclopentanol, 1-methylcyclohexanol, 1-ethylcyclohexanol, 1-propylcyclopentanol, 2-methyladamantanol, 3-phenyl-3-pentanol, 2-phenyl-2-butanol, 2-methyl-1-phenyl-2-propanol, 2-methyl-1-phenyl-2-butanol, 3-benzyl-3-hexanol, 2-α-naphthyl-2-propanol, and 2-methyl-1-β-naphthyl-2-propanol, preferably tert-butanol, 2-methyl-2-butanol, 2-methyl-2-pentanol, 3-methyl-3-pentanol, 3-ethyl-3-pentanol, 2-methyl-3-buten-2-ol, and 2-methyl-1-phenyl-2-propanol, and further preferably tert-butanol, 2-methyl-2-butanol, 2-methyl-3-buten-2-ol, and 2-methyl-1-phenyl-2-propanol. These tertiary alcohols may be used singly or in combination of two or more in an arbitrary ratio. "tert-Butanol" is also referred to as "tert-butyl alcohol."

The amount of the tertiary alcohol used in step (i) may be an arbitrary amount as long as the reaction proceeds. However, in view of yield, by-product suppression, economic efficiency, and the like, when the base is an alkali metal hydride (preferably sodium hydride), the amount of the tertiary alcohol used in step (i) is, for example, 0.3 equivalents or more, preferably 0.3 equivalents to 4.0 equivalents, more preferably 0.4 equivalents to 2.1 equivalents, further preferably 0.5 equivalents to 2.0 equivalents, and further preferably 0.5 equivalents to 1.5 equivalents per 1 equivalent of the compound of the formula (2) (aniline compound), in one aspect, and preferably 0.4 equivalents to 3.2 equivalents, further preferably 0.9 equivalents to 2.1 equivalents, and further preferably 1.0 equivalent to 2.0 equivalents in another aspect.

From the same viewpoint as the above, when the base is an alkali metal amide (preferably lithium amide), the amount of the tertiary alcohol used in step (i) is, for example, 0.3 equivalents or more, preferably 0.3 equivalents to 4.0 equivalents, more preferably 0.3 equivalents to 2.5 equivalents, further preferably 0.5 equivalents to 2.0 equivalents, and further preferably 0.5 equivalents to 1.5 equivalents per 1 equivalent of the compound of the formula (2) (aniline compound), in one aspect, and preferably 0.4 equivalents to 1.1 equivalents in another aspect.

When the base comprises a plurality of compounds, the amount of the tertiary alcohol used in step (i) is, for example, 0.3 equivalents or more, preferably 0.3 equivalents to 4.0 equivalents, and more preferably 0.3 equivalents to 2.5 equivalents per 1 equivalent of the compound of the formula (2) (aniline compound), in one aspect, and, for example, 0.5 equivalents to 2.5 equivalents, preferably 0.5 equivalents to 2.0 equivalents, and further preferably 0.5 equivalents to 1.5 equivalents, in another aspect.

As described above, the definition of "the equivalent of the tertiary alcohol" as used herein is as follows, or the term "equivalent" is construed according to the following examples. For example, "1 equivalent of tert-butanol per 1 equivalent of the compound of the formula (2) (aniline compound)" means "1 mol of tert-butanol per 1 mol of the compound of the formula (2) (aniline compound)." For example, "0.5 equivalents of tert-butanol per 1 equivalent of the compound of the formula (2) (aniline compound)" means "0.5 mol of tert-butanol per 1 mol of the compound of the formula (2) (aniline compound)."

A predetermined amount of the tertiary alcohol used can be added to the reaction at once. Alternatively, the tertiary alcohol may be added in a plurality of portions or by dropping.

(Solvent in Step (i))

In view of the smooth progress of the reaction, and the like, the reaction in step (i) is preferably performed in the presence of a solvent. Examples of the solvent in step (i) include, but are not limited to, the following; aromatic hydrocarbon derivatives (for example, benzene, toluene, xylene, chlorobenzene, and dichlorobenzene), halogenated aliphatic hydrocarbons (for example, dichloromethane and 1,2-dichloroethane), ethers (for example, diethyl ether, diisopropyl ether, cyclopentyl methyl ether (CPME), tetrahydrofuran (THF), 1,4-dioxane, monoglyme, and diglyme), amides (for example, N,N-dimethylformamide (DMF), N,N-dimethylacetamide (DMAC), and N-methylpyrrolidone (NMP)), sulfoxides (for example, dimethyl sulfoxide (DMSO)), and any combination thereof in an arbitrary ratio.

The solvent in step (i) may be any solvent as long as the reaction in step (i) proceeds. However, in view of yield, by-product suppression, economic efficiency, and the like, preferred examples of the solvent in step (i) include toluene, xylene, chlorobenzene, dichlorobenzene, dichloromethane, tetrahydrofuran (THF), N,N-dimethylformamide (DMF), and any combination thereof in an arbitrary ratio, more preferably toluene, xylene, chlorobenzene, and dichlorobenzene, further preferably toluene and xylene, and further preferably toluene.

The amount of the solvent used in step (i) may be an arbitrary amount as long as the reaction system can be sufficiently stirred. In view of yield, by-product suppression, economic efficiency, and the like, an exemplary range is 10 L (liters) or less, preferably 0.1 to 10 L, more preferably 0.1 to 5 L, and further preferably 0.5 to 5 L per 1 mol of the compound of the formula (2) (aniline compound).

(Reaction Temperature in Step (i))

In view of yield, by-product suppression, economic efficiency, and the like, when the base is an alkali metal hydride (preferably sodium hydride), the reaction temperature in step (i) is, for example, −5° C. (minus 5° C.) to 80° C., preferably −5° C. to 50° C., more preferably 0° C. to 50° C., and further preferably 0° C. to 40° C., in one aspect, and, for example, 0° C. to 80° C., preferably 10° C. to 80° C., more preferably 20° C. to 70° C., further preferably 20° C. to 40° C., and most preferably 25° C. to 35° C., in another aspect.

From the same viewpoint as the above, when the base is an alkali metal amide (preferably lithium amide), the reaction temperature in step (i) is, for example, −5° C. (minus 5° C.) to 80° C., preferably −5° C. to 50° C., more preferably 0° C. to 50° C., and further preferably 0° C. to 40° C., in one aspect, and, for example, −20° C. (minus 20° C.) to 60° C., preferably −10° C. to 40° C., more preferably 0° C. to 30° C., and further preferably 0° C. to 15° C., in another aspect.

When the base comprises a plurality of compounds, the reaction temperature in step (i) is, for example, −5° C. (minus 5° C.) to 80° C., preferably −5° C. to 50° C., more preferably 0° C. to 50° C., and further preferably 0° C. to 40° C. in one aspect, and is, for example, 0° C. to 80° C., more preferably 0° C. to 60° C., further preferably 10° C. to 80° C., further preferably 20° C. to 70° C., further preferably 20° C. to 40° C., and most preferably 25° C. to 35° C. in another aspect. It is, for example, −20° C. (minus 20° C.) to 60° C., preferably −10° C. to 40° C., more preferably 0° C. to 30° C., and further preferably 0° C. to 15° C. in still another aspect.

(Reaction Time in Step (i))

The reaction time in step (i) is not particularly limited. However, in view of yield, by-product suppression, economic efficiency, and the like, the reaction time is, for example, 0.1 h to 48 h, preferably 1 h to 48 h, more preferably 1 h to 36 h, and further preferably 1 h to 24 h.

The compound of the formula (3) can be used as a raw material in step (ii). The compound of the formula (3) may be isolated and used in the next step, further purified and used in the next step, or used in the next step without isolation, as long as the reaction in step (ii) proceeds. In addition, after the completion of the reaction in step (i), hydrochloric acid or acetic acid may be used, for example, for post-treatment in step (i). Additionally, after the completion of the reaction in step (i), an inert gas such as nitrogen may be blown into the solution to remove the by-products (as post-treatment in step (i)). The removal of the by-products may be performed under reduced pressure. Examples of the by-products include ammonia.

(Product in Step (i); Compound of Formula (3), which is Nitroso Compound)

Specific examples of the compound of the formula (3) obtained in step (i) include, but are not limited to, the following;
3-chloro-N-(4-methoxyphenyl)-2-nitrosoaniline,
N-(4-methoxyphenyl)-2-nitrosoaniline, and
3-chloro-2-nitroso-N-phenylaniline.

In view of the usefulness of the product, and the like, preferred specific examples of the compound of the formula (3) include the following;
3-chloro-N-(4-methoxyphenyl)-2-nitrosoaniline and
N-(4-methoxyphenyl)-2-nitrosoaniline.

From the same viewpoint as the above, a preferred specific example of the compound of the formula (3) is the following;
3-chloro-N-(4-methoxyphenyl)-2-nitrosoaniline.

(Step (ii))

Step (ii) will be described.

Step (ii) is the step of reacting the compound of the formula (3) with a compound of a formula (4) to produce a compound of a formula (5).

[Formula 26]

(3)

-continued (4)

(5)

wherein $R^1$, $R^2$, $R^3$, $R^4$, R, R, $R^7$, $R^8$, $R^9$, $R^{10}$, $R^{11}$, and $R^{12}$ are as defined above.

(Raw Material; Malonic Acid Diester Compound)

As a raw material in step (ii), the compound of the formula (4), which is a malonic acid diester compound, is used. The compound of the formula (4) is a known compound or can be produced from a known compound according to a known method.

Examples of the compound of the formula (4) include, but are not limited to, dimethyl malonate, diethyl malonate, dipropyl malonate, diisopropyl malonate, dibutyl malonate, diisobutyl malonate, and di-t-butyl malonate, preferably dimethyl malonate and diethyl malonate.

The amount of the compound of the formula (4) used may be an arbitrary amount as long as the reaction proceeds. The amount of the compound of the formula (4) used can be suitably adjusted by those skilled in the art. However, in view of yield, by-product suppression, economic efficiency, and the like, the amount of the compound of the formula (4) used is 1.0 mol to 3.0 mol, preferably 1.0 mol to 2.0 mol, and more preferably 1.0 mol to 1.5 mol per 1 mol of the compound of the formula (3) (nitroso compound).

(Conditions in Step (ii))

The reaction in step (ii) is preferably performed under basic conditions. In one aspect, the reaction in step (ii) is usually performed at pH 9 or more, preferably pH 9 to pH 20, and more preferably pH 9 to pH 14. In another aspect, the reaction in step (ii) is performed at pH 8 or more, preferably pH 8 to pH 20, and more preferably pH 8 to pH 14. In still another aspect, the reaction in step (ii) is performed at pH 8 to pH 12, preferably pH 9 to pH 12, and more preferably pH 10 to pH 12. Therefore, the pH may be adjusted before the reaction in step (ii). For the adjustment of the pH, an acidic substance is used, and, for example, acetic acid and hydrochloric acid can be used. The amount of the acid used is an amount with which the desired pH is obtained. Therefore, the amount of the acid used can be suitably adjusted by those skilled in the art. In addition, the reaction in step (ii) may be performed in the presence of a base. The base used in step (ii) may be any base as long as the reaction proceeds.

Examples of the base in step (ii) include, but are not limited to, the following;
alkali metal hydroxides (for example, lithium hydroxide, sodium hydroxide, and potassium hydroxide), alkaline earth metal hydroxides (for example, magnesium hydroxide, calcium hydroxide, and barium hydroxide),
alkali metal carbonates (for example, lithium carbonate, potassium carbonate, sodium carbonate, and cesium carbonate),
alkaline earth metal carbonates (for example, magnesium carbonate, calcium carbonate, and barium carbonate),
alkali metal hydrogen carbonates (for example, lithium hydrogen carbonate, and sodium hydrogen carbonate),
alkaline earth metal hydrogen carbonates (for example, calcium hydrogen carbonate), and
organic bases (for example, triethylamine, diisopropylethylamine, 1,8-diazabicyclo[5.4.0]-7-undec-7-ene (DBU), 1,5-diazabicyclo[4.3.0]non-5-ene (DBN), 1,4-diazabicyclo[2.2.2]octane (DABCO), pyridine, and N,N-dimethyl-4-aminopyridine).

In view of yield, by-product suppression, economic efficiency, and the like, preferred specific examples of the base in step (ii) include lithium hydroxide, sodium hydroxide, potassium hydroxide, potassium carbonate, and triethylamine.

These bases in step (ii) may be used singly or in combination of two or more in an arbitrary ratio. The form of the base in step (ii) may be any form as long as the reaction proceeds. The form of the base in step (ii) can be suitably selected by those skilled in the art.

The amount of the base used in step (ii) may be an arbitrary amount as long as the reaction proceeds. However, in view of yield, by-product suppression, economic efficiency, and the like, the amount of the base used in step (ii) is, for example, usually 1 equivalent or more, preferably 1 equivalent to 20 equivalents, more preferably 1 equivalent to 15 equivalents, and further preferably 1 equivalent to 10 equivalents per 1 equivalent of the compound of the formula (3) (nitroso compound). However, the amount of the base used in step (ii) can be suitably adjusted by those skilled in the art.

The reaction in step (ii) can be performed in the presence or absence of a phase transfer catalyst. Whether a phase transfer catalyst is used or not can be suitably determined by those skilled in the art. Examples of the phase transfer catalyst include, but are not limited to, quaternary ammonium salts (for example, tetrabutylammonium bromide (TBAB), tetrabutylammonium hydrogen sulfate, and trimethylbenzylammonium chloride), quaternary phosphonium salts (for example, tetrabutylphosphonium bromide, tetraoctylphosphonium bromide, and tetraphenylphosphonium bromide), and crown ethers (for example, 12-crown-4, 15-crown-5, and 18-crown-6).

When a phase transfer catalyst is used in step (ii), the amount of the phase transfer catalyst used in step (ii) is, for example, usually 0.001 mol to 0.5 mol, preferably 0.005 mol to 0.3 mol, per 1 mol of the compound of the formula (3) (nitroso compound).

(Water in Step (ii))
The reaction in step (ii) can be performed in the presence or absence of water. However, the reaction in step (ii) is preferably performed in the presence of water. The amount of water used in step (ii) is, for example, usually 0.5 mol to 10.0 mol, preferably 1.0 mol to 5.0 mol, per 1 mol of the compound of the formula (3) (nitroso compound). Water may be added alone or derived from the hydrochloric acid used in the above pH adjustment.

(Solvent in Step (ii))
In view of the smooth progress of the reaction, and the like, the reaction in step (i) is preferably performed in the presence of a solvent. The solvent, the amount of the solvent used, and the like in step (ii) may be the same as those in step (ii). In addition, water may be present.

(Reaction Temperature in Step (ii))
The reaction temperature in step (ii) is not particularly limited. However, in view of yield, by-product suppression, economic efficiency, and the like, the reaction temperature is, for example, $-10°$ C. to $80°$ C., preferably $0°$ C. to $60°$ C., more preferably $0°$ C. to $30°$ C., and further preferably $0°$ C. to $20°$ C.

(Reaction Time in Step (ii))
The reaction time in step (ii) is not particularly limited. In view of yield, by-product suppression, economic efficiency, and the like, the reaction time is, for example, 0.1 h to 48 h, preferably 0.1 h to 24 h, and more preferably 0.5 h to 15 h.

(Post-Treatment and Purification)
The production of a carboxylate with a base or a salt, and/or the production of a free carboxylic acid with an acid can be performed. For example, operations such as the extraction of the product with water, the extraction of the product with an organic solvent, crystal precipitation with an acid, and crystal precipitation with a base may be performed. For example, an aqueous solution including the target sodium carboxylate or lithium carboxylate, or the like may be treated with an acid to precipitate crystals of the target free carboxylic acid. The target sodium carboxylate or lithium carboxylate may be extracted with water. An organic solvent solution including the target free carboxylic acid, or the like may be treated with a base to precipitate crystals of the target sodium carboxylate or lithium carboxylate. An aqueous solution including the target sodium carboxylate or lithium carboxylate, or the like may be treated with a potassium salt or calcium salt to precipitate crystals of the potassium carboxylate or calcium carboxylate. The target free carboxylic acid may be extracted with an organic solvent.

Further, in some cases, the target sodium carboxylate or lithium carboxylate or the target free carboxylic acid, or an aqueous solution or organic solvent solution thereof may be washed with water or an organic solvent or any mixed solvent thereof in an arbitrary ratio suitably selected. Further, in some cases, the recovery of the solvent may be performed. For example, the solvent used in the reaction may be recovered, and the solvent used in the post-treatment and purification may be recovered.

(Product in Step (ii); Compound of Formula (5), which is Quinoxaline Compound)
Specific examples of the compound of the formula (5) obtained in step (ii) include, but are not limited to, the following;

5-chloro-1-(4-methoxyphenyl)-2-oxo-1,2-dihydroquinoxaline-3-carboxylic acid,
5-chloro-1-(4-ethoxyphenyl)-2-oxo-1,2-dihydroquinoxaline-3-carboxylic acid,
5-chloro-1-(4-propoxyphenyl)-2-oxo-1,2-dihydroquinoxaline-3-carboxylic acid,
5-chloro-1-(4-isopropoxyphenyl)-2-oxo-1,2-dihydroquinoxaline-3-carboxylic acid,
5-chloro-1-(4-butoxyphenyl)-2-oxo-1,2-dihydroquinoxaline-3-carboxylic acid,
5-chloro-1-(4-t-butoxyphenyl)-2-oxo-1,2-dihydroquinoxaline-3-carboxylic acid,
5-chloro-1-(4-methylphenyl)-2-oxo-1,2-dihydroquinoxaline-3-carboxylic acid,
5-chloro-1-(4-ethylphenyl)-2-oxo-1,2-dihydroquinoxaline-3-carboxylic acid,
5-chloro-1-(4-propylphenyl)-2-oxo-1,2-dihydroquinoxaline-3-carboxylic acid, 5-chloro-1-(4-isopropylphenyl)-2-oxo-1,2-dihydroquinoxaline-3-carboxylic acid,
5-chloro-1-(4-butylphenyl)-2-oxo-1,2-dihydroquinoxaline-3-carboxylic acid,
5-chloro-1-(4-t-butylphenyl)-2-oxo-1,2-dihydroquinoxaline-3-carboxylic acid,
5-chloro-1-phenyl-2-oxo-1,2-dihydroquinoxaline-3-carboxylic acid,
1-(4-methoxyphenyl)-2-oxo-1,2-dihydroquinoxaline-3-carboxylic acid,
1-(4-ethoxyphenyl)-2-oxo-1,2-dihydroquinoxaline-3-carboxylic acid,
1-(4-propoxyphenyl)-2-oxo-1,2-dihydroquinoxaline-3-carboxylic acid,
1-(4-isopropoxyphenyl)-2-oxo-1,2-dihydroquinoxaline-3-carboxylic acid,
1-(4-butoxyphenyl)-2-oxo-1,2-dihydroquinoxaline-3-carboxylic acid,
1-(4-t-butoxyphenyl)-2-oxo-1,2-dihydroquinoxaline-3-carboxylic acid,
1-(4-methylphenyl)-2-oxo-1,2-dihydroquinoxaline-3-carboxylic acid,
1-(4-ethylphenyl)-2-oxo-1,2-dihydroquinoxaline-3-carboxylic acid,
1-(4-propylphenyl)-2-oxo-1,2-dihydroquinoxaline-3-carboxylic acid,
1-(4-isopropylphenyl)-2-oxo-1,2-dihydroquinoxaline-3-carboxylic acid,
1-(4-butylphenyl)-2-oxo-1,2-dihydroquinoxaline-3-carboxylic acid,
1-(4-t-butylphenyl)-2-oxo-1,2-dihydroquinoxaline-3-carboxylic acid,
1-phenyl-2-oxo-1,2-dihydroquinoxaline-3-carboxylic acid, and
potassium salts, sodium salts, lithium salts, methyl esters, and ethyl esters thereof.

In view of the usefulness of the product, and the like, preferred specific examples of the compound of the formula (5) include the following;
5-chloro-1-(4-methoxyphenyl)-2-oxo-1,2-dihydroquinoxaline-3-carboxylic acid and
1-(4-methoxyphenyl)-2-oxo-1,2-dihydroquinoxaline-3-carboxylic acid,
more preferably 5-chloro-1-(4-methoxyphenyl)-2-oxo-1,2-dihydroquinoxaline-3-carboxylic acid.

EXAMPLES

The present invention will be described in more detail by following Examples, but the present invention is not limited by these Examples in any way.

As used herein, room temperature is 10° C. to 35° C.

Herein, for the measurement of the physical properties and yield in the Examples and Comparative Examples, the following equipment can be used. In addition, the products obtained in the present invention are known compounds, and were identified and quantified by ordinary methods known to those skilled in the art.
Measurement of pH; type: HM-20P or HM-30P (manufactured by DKK-TOA CORPORATION) as glass electrode type hydrogen ion concentration indicator, and model: 3200 (manufactured by Agilent Technologies Japan, Ltd.) as electrochemical meter.

High performance liquid chromatography (HPLC) analysis; type: LC-2010A HT (manufactured by SHIMADZU CORPORATION).

"OCNB" means "2-chloronitrobenzene" as shown below.

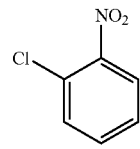

[Formula 27]

"p-A" means "p-anisidine" as shown below.

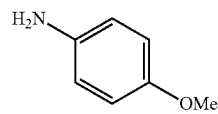

[Formula 28]

"MNA" means "N-(4-methoxyphenyl)-2-nitroaniline" as shown below.

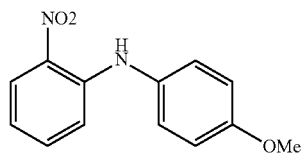

[Formula 29]

"CMNA" means "3-chloro-N-(4-methoxyphenyl)-2-nitroaniline" as shown below.

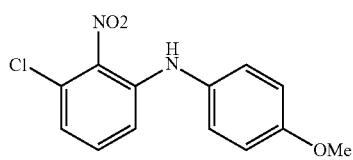

[Formula 30]

"DMM" means "dimethyl malonate" as shown below.

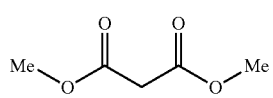

[Formula 31]

"DEM" means "diethyl malonate" as shown below.

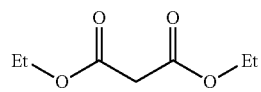

[Formula 32]

"CAQ" means "5-chloro-1-(4-methoxyphenyl)-2-oxo-1,2-dihydroquinoxaline-3-carboxylic acid" as shown below.

[Formula 33]

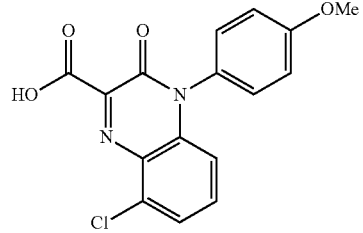

Example 1

Production of 3-Chloro-N-(4-methoxyphenyl)-2-nitrosoaniline

[Formula 34]

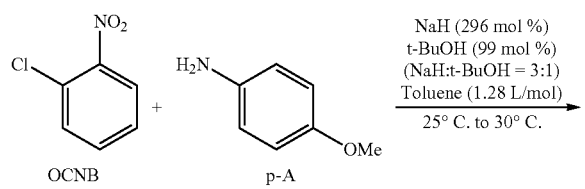

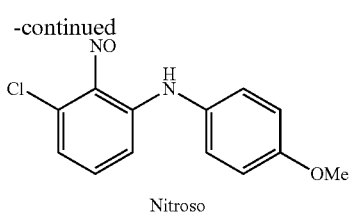

Nitroso

Sodium hydride (purity: 65.1%, liquid paraffin-dispersed, 5.5 g, 149.2 mmol, 296 mol %) was suspended in toluene (28.0 g, 0.64 L/mol) under a nitrogen gas flow. A toluene (14.0 g, 0.32 L/mol) solution of tert-butanol (3.71 g, 50.1 mmol, 99 mol %) was dropped thereinto at an internal temperature of 55 to 60° C. over 30 min, and then the mixture was stirred at the same temperature for 30 min. The internal temperature was cooled to 25 to 30° C., and a solution of p-anisidine (6.2 g, 50.3 mmol, 100 mol %) and 2-chloronitrobenzene (7.9 g, 50.1 mmol, 100 mol %) dissolved in toluene (14.0 g, 0.32 L/mol) was dropped thereinto over 1 h. The mixture was stirred at the same temperature for 20 h.

As a result of the HPLC analysis (area percentage; 254 nm) of the reaction mixture, the main components in the reaction mixture excluding the solvent and the like were as follows; 3-chloro-N-(4-methoxyphenyl)-2-nitrosoaniline (target product): 50.7%, OCNB (raw material): 0.6%, p-anisidine (raw material): 0.1%

MNA (by-product; compound by substitution of Cl (compound by elimination of Cl)): 31.1%, CMNA (by-product; nitro derivative corresponding of target product): 2.4%.

The reaction mixture was analyzed by the HPLC absolute calibration curve method to obtain the yield and the like. The results of the analysis were as follows; 3-chloro-N-(4-methoxyphenyl)-2-nitrosoaniline (target product): 53.5% (yield), OCNB (raw material): 0.8% (recovery rate), MNA (by-product; compound by substitution of Cl (compound by elimination of Cl)): 25.0%.

Examples 2 to 4

A reaction and analysis were performed in the same manner as Example 1 except that the amount of tert-butanol was changed as shown in Table 1. The results are shown in Table 1. In addition, the results of Example 1 are also summarized in Table 1.

TABLE 1

| Example No | Base | Base (equivalents) | t-BuOH (equivalents) | Area % of HPLC (254 nm) | | | | | Yield (%) | | |
| | | | | Target product | OCNB | p-Anisidine | MNA | CMNA | Target product | OCNB | MNA |
| --- | --- | --- | --- | --- | --- | --- | --- | --- | --- | --- | --- |
| 1 | NaH | 3.0 | 1.0 | 50.7 | 0.6 | 0.1 | 31.1 | 2.4 | 53.5 | 0.8 | 25.0 |
| 2 | NaH | 3.0 | 0.5 | 48.5 | 1.2 | 0.2 | 31.9 | 1.9 | 49.6 | 2.1 | 24.8 |
| 3 | NaH | 3.0 | 2.0 | 55.9 | 3.0 | 0.4 | 26.1 | 1.8 | 50.2 | 5.2 | 17.8 |
| 4 | NaH | 3.0 | 3.1 | 49.7 | 6.8 | 0.9 | 25.9 | 2.2 | 48.2 | 19.7 | 17.0 |

Example 5

Production of 3-Chloro-N-(4-methoxyphenyl)-2-nitrosoaniline

[Formula 35]

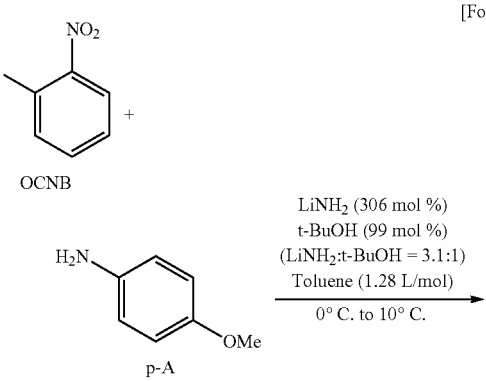

-continued

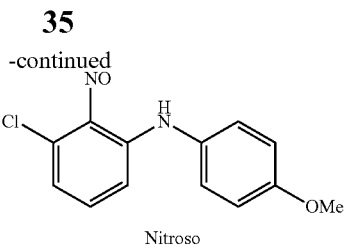

Nitroso

Lithium amide (purity: 95.0%, 3.72 g, 153.9 mmol, 306 mol %) was suspended in toluene (28.0 g, 0.64 L/mol) under a nitrogen gas flow. A toluene (14.0 g, 0.32 L/mol) solution of tert-butanol (3.7 g, 49.9 mmol, 99 mol %) was dropped thereinto at an internal temperature of 0 to 10° C. over 30 min, and then the mixture was stirred at the same temperature for 30 min. The internal temperature was maintained at the same temperature, and a solution of p-anisidine (6.2 g, 50.3 mmol, 100 mol %) and 2-chloronitrobenzene (7.9 g, 50.1 mmol, 100 mol %) dissolved in toluene (14.0 g, 0.32 L/mol) was dropped thereinto over 1 h. The mixture was stirred at the same temperature for 20 h.

As a result of the HPLC analysis (area percentage; 254 nm) of the reaction mixture, the main components in the reaction mixture excluding the solvent and the like were as follows; 3-chloro-N-(4-methoxyphenyl)-2-nitrosoaniline (target product): 67.6%,
OCNB (raw material): 11.2%,
p-anisidine (raw material): 1.7%
MNA (by-product; compound by substitution of Cl (compound by elimination of Cl)): 6.6%,
CMNA (by-product; nitro derivative corresponding of target product): 3.0%.

The reaction mixture was analyzed by the HPLC absolute calibration curve method to obtain the yield and the like. The results of the analysis were as follows;
3-chloro-N-(4-methoxyphenyl)-2-nitrosoaniline (target product): 74.9% (yield),
OCNB (raw material): 4.3% (recovery rate),
MNA (by-product; compound by substitution of Cl (compound by elimination of Cl)): 2.8%.

Examples 6 to 10

A reaction and analysis were performed in the same manner as Example 5 except that the amount of lithium amide and the amount of tert-butanol were changed as shown in Table 2. The results are shown in Table 2. In addition, the results of Example 5 are also summarized in Table 2. It is seen that the yield increases by suitably adjusting the amounts of the base and tert-butanol used.

Example 11

Production of 3-Chloro-N-(4-methoxyphenyl)-2-nitrosoaniline

[Formula 36]

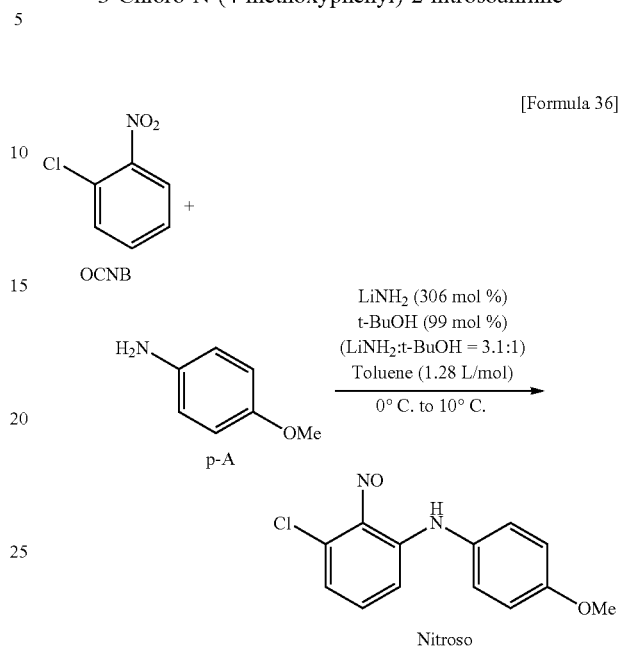

Lithium amide (purity: 95.0%, 3.72 g, 153.9 mmol, 306 mol %) was suspended in toluene (10.0 g, 0.23 L/mol) under a nitrogen gas flow. A toluene (2.0 g, 0.05 L/mol) solution of tert-butanol (3.7 g, 49.9 mmol, 99 mol %) was dropped thereinto at an internal temperature of 0 to 10° C. over 30 min, and then the mixture was stirred at the same temperature for 30 min. The internal temperature was maintained at the same temperature, a solution of 2-chloronitrobenzene (7.9 g, 50.1 mmol, 100 mol %) dissolved in toluene (2.0 g, 0.05 L/mol) was added thereto, and then a solution of p-anisidine (6.2 g, 50.3 mmol, 100 mol %) dissolved in toluene (42.0 g, 0.96 L/mol) was dropped over 3 h. The mixture was stirred at the same temperature for 20 h.

As a result of the HPLC analysis (area percentage; 254 nm) of the reaction mixture, the main components in the reaction mixture excluding the solvent and the like were as follows; 3-chloro-N-(4-methoxyphenyl)-2-nitrosoaniline (target product): 80.9%,
OCNB (raw material): 1.1%,
p-anisidine (raw material): 0.2%

TABLE 2

| Example No | Base | Base (equivalents) | t-BuOH (equivalents) | Area % of HPLC (254 nm) | | | | | Yield (%) | | |
| | | | | Target product | OCNB | p-Anisidine | MNA | CMNA | Target product | OCNB | MNA |
| --- | --- | --- | --- | --- | --- | --- | --- | --- | --- | --- | --- |
| 5 | LiNH$_2$ | 3.1 | 1.0 | 67.6 | 11.2 | 1.7 | 6.6 | 3.0 | 74.9 | 4.3 | 2.8 |
| 6 | LiNH$_2$ | 3.1 | 0.5 | 70.5 | 2.5 | 0.1 | 12.4 | 3.6 | 71.9 | 1.0 | 7.7 |
| 7 | LiNH$_2$ | 3.1 | 1.5 | 67.5 | 13.1 | 1.8 | 6.4 | 3.4 | 56.1 | 29.5 | 2.1 |
| 8 | LiNH$_2$ | 3.1 | 2.0 | 68.5 | 20.6 | 3.6 | 2.4 | 1.7 | 49.2 | 40.6 | N.D |
| 9 | LiNH$_2$ | 3.1 | 2.5 | 64.2 | 27.0 | 3.9 | 0.9 | 0.8 | 41.9 | 55.3 | N.D |
| 10 | LiNH$_2$ | 2.6 | 0.5 | 69.0 | 2.8 | 0.5 | 11.5 | 4.4 | 51.6 | 24.1 | 2.5 |

N.D = Not Detected

MNA (by-product; compound by substitution of Cl (compound by elimination of Cl)): 5.2%,
CMNA (by-product; nitro derivative corresponding of target product): 3.4%.

The reaction mixture was analyzed by the HPLC absolute calibration curve method to obtain the yield and the like. The results of the analysis were as follows; 3-chloro-N-(4-methoxyphenyl)-2-nitrosoaniline (target product): 75.0% (yield),
OCNB (raw material): trace (recovery rate),
MNA (by-product; compound by substitution of Cl (compound by elimination of Cl)): 1.9%.

Example 12

Production of 3-Chloro-N-(4-methoxyphenyl)-2-nitrosoaniline

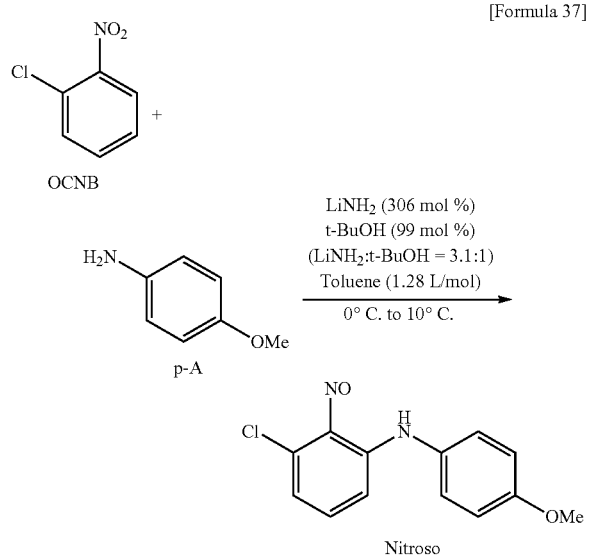

[Formula 37]

Lithium amide (purity: 95.0%, 3.72 g, 153.9 mmol, 306 mol %) was suspended in toluene (10.0 g, 0.23 L/mol) under a nitrogen gas flow. A toluene (2.0 g, 0.05 L/mol) solution of tert-butanol (3.7 g, 49.9 mmol, 99 mol %) was dropped thereinto at an internal temperature of 0 to 10° C. over 30 min, and then the mixture was stirred at the same temperature for 30 min. The internal temperature was maintained at the same temperature, a solution of 2-chloronitrobenzene (11.8 g, 74.9 mmol, 149 mol %) dissolved in toluene (2.0 g, 0.05 L/mol) was added thereto, and then a solution of p-anisidine (6.2 g, 50.3 mmol, 100 mol %) dissolved in toluene (42.0 g, 0.96 L/mol) was dropped over 1 h. The mixture was stirred at the same temperature for 20 h.

As a result of the HPLC analysis (area percentage; 254 nm) of the reaction mixture, the main components in the reaction mixture excluding the solvent and the like were as follows; 3-chloro-N-(4-methoxyphenyl)-2-nitrosoaniline (target product): 73.5%,
OCNB (raw material): 14.4%,
p-anisidine (raw material): 0.3%
MNA (by-product; compound by substitution of Cl (compound by elimination of Cl)): 3.3%,
CMNA (by-product; nitro derivative corresponding of target product): 2.1%.

The reaction mixture was analyzed by the HPLC absolute calibration curve method to obtain the yield and the like. The results of the analysis were as follows;
3-chloro-N-(4-methoxyphenyl)-2-nitrosoaniline (target product): 84.1% (yield),
OCNB (raw material): 48.0% (recovery rate),
MNA (by-product; compound by substitution of Cl (compound by elimination of Cl)): 1.1%.

Example 13

Production of N-(4-methoxyphenyl)-2-nitrosoaniline

[Formula 38]

Sodium hydride (purity: 65.1%, liquid paraffin-dispersed, 5.5 g, 149.2 mmol, 298 mol %) was suspended in toluene (28.0 g, 0.65 L/mol) under a nitrogen gas flow. A toluene (14.0 g, 0.32 L/mol) solution of tert-butanol (3.7 g, 49.9 mmol, 100 mol %) was dropped thereinto at an internal temperature of 55° C. to 60° C. over 30 min, and then the mixture was stirred at the same temperature for 30 min. The internal temperature was cooled to 25 to 30° C., and a solution of p-anisidine (6.2 g, 50.0 mmol, 100 mol %) and nitrobenzene (6.2 g, 50.0 mmol, 100 mol %) dissolved in toluene (14.0 g, 0.32 L/mol) was dropped thereinto over 1 h. The mixture was stirred at the same temperature for 20 h.

As a result of the HPLC analysis (area percentage; 254 nm) of the reaction mixture, the main components in the reaction mixture excluding the solvent and the like were as follows;

N-(4-methoxyphenyl)-2-nitrosoaniline (target product): 56.1%,
nitrobenzene (raw material): 20.8%,
p-anisidine (raw material): 0.7%.

The reaction mixture was analyzed by the HPLC absolute calibration curve method to obtain the yield and the like. The results of the analysis were as follows; N-(4-methoxyphenyl)-2-nitrosoaniline (target product): 51.3% (yield),
nitrobenzene (raw material): 18.4% (recovery rate).

Example 14

Production of N-(4-Methoxyphenyl)-2-nitrosoaniline

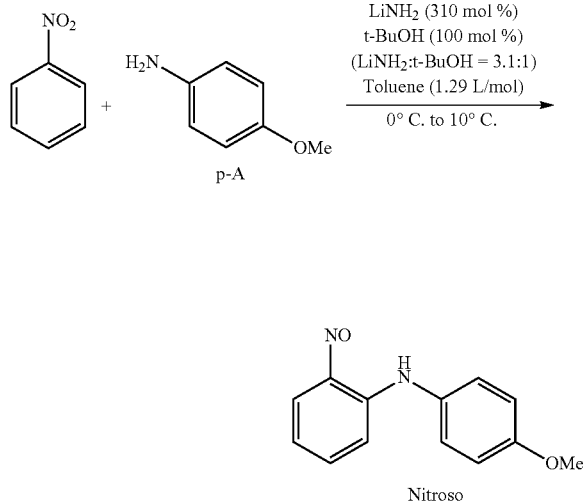

[Formula 39]

Lithium amide (purity: 95.0%, 3.75 g, 155.2 mmol, 310 mol %) was suspended in toluene (28.1 g, 0.65 L/mol) under a nitrogen gas flow. A toluene (14.0 g, 0.32 L/mol) solution of tert-butanol (3.71 g, 50.1 mmol, 100 mol %) was dropped thereinto at an internal temperature of 0 to 10° C. over 30 min, and then the mixture was stirred at the same temperature for 30 min. The internal temperature was maintained at the same temperature, and a solution of p-anisidine (6.2 g, 50.0 mmol, 100 mol %) and nitrobenzene (6.2 g, 50.0 mmol, 100 mol %) dissolved in toluene (14.0 g, 0.32 L/mol) was dropped thereinto over 1 h. The mixture was stirred at the same temperature for 20 h.

As a result of the HPLC analysis (area percentage; 254 nm) of the reaction mixture, the main components in the reaction mixture excluding the solvent and the like were as follows;

N-(4-methoxyphenyl)-2-nitrosoaniline (target product): 55.1%, nitrobenzene (raw material): 12.7%, p-anisidine (raw material): 0.5%.

The reaction mixture was analyzed by the HPLC absolute calibration curve method to obtain the yield and the like. The results of the analysis were as follows;

N-(4-methoxyphenyl)-2-nitrosoaniline (target product): 44.6% (yield), nitrobenzene (raw material): 30.3% (recovery rate).

According to Examples 1 to 14, the target nitroso compound can be obtained without requiring extreme low temperature. In addition, according to Examples 1 to 14, the amount of the aniline compound, a raw material, used can be reduced.

Example 15

Production of 5-Chloro-1-(4-methoxyphenyl)-2-oxo-1,2-dihydroquinoxaline-3-carboxylic Acid

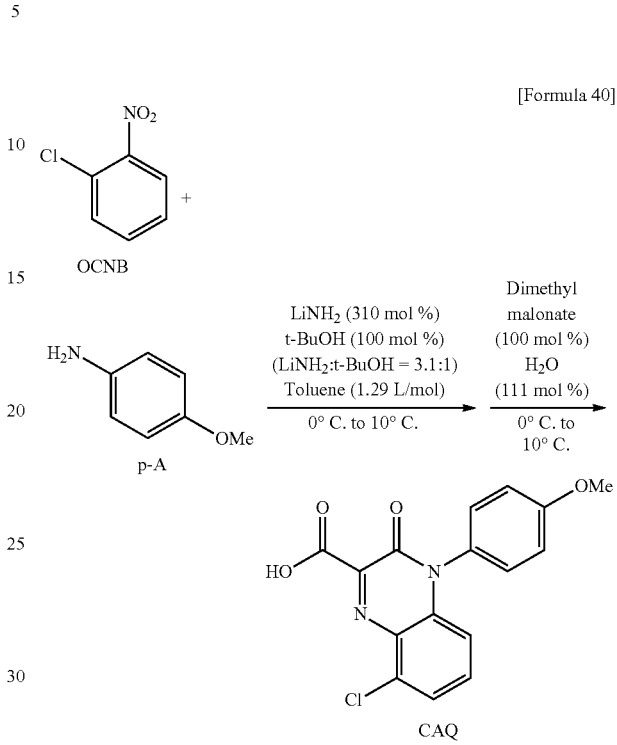

[Formula 40]

Step (i)

Lithium amide (purity: 95.0%, 7.50 g, 310.3 mmol, 311 mol %) was suspended in toluene (56.1 g, 0.65 L/mol) under a nitrogen gas flow. A toluene (28.0 g, 0.32 L/mol) solution of tert-butanol (7.4 g, 99.8 mmol, 100 mol %) was dropped thereinto at an internal temperature of 0 to 10° C. over 30 min, and then the mixture was stirred at the same temperature for 30 min. A solution of p-anisidine (12.3 g, 99.9 mmol, 100 mol %) and 2-chloronitrobenzene (15.8 g, 100.3 mmol, 100 mol %) dissolved in toluene (28.0 g, 0.32 L/mol) was dropped thereinto over 1 h. The mixture was stirred at the same temperature for 20 h. A reaction mixture including target intermediate 3-chloro-N-(4-methoxyphenyl)-2-nitrosoaniline was obtained.

Step (ii)

Water (1.8 g, 99.9 mmol, 100 mol % (based on p-anisidine)) was dropped into the reaction mixture obtained in the above step (i) at an internal temperature of 0 to 10° C. Then diethyl malonate (16.0 g, 99.9 mmol, 100 mol % (based on p-anisidine)) was dropped at the same temperature over 1 h, and the mixture was stirred at the same temperature for 2 h. Water (0.2 g) was added thereto, and the mixture was further stirred for 2 h.

4% hydrochloric acid (231.8 g) was dropped thereinto to adjust the pH of the solution at 9.5. The internal temperature was increased to 35 to 40° C., and the mixture was divided into toluene and water. The toluene phase was removed. The obtained aqueous phase was washed with toluene (43.5 g×twice), and then 35% hydrochloric acid (31.9 g) was dropped into the aqueous phase at an internal temperature of 25 to 30°. The mixture was stirred for 30 min, and then the crystals were filtered. The crystals were washed with toluene (19.8 g) and water (25.0 g). The obtained crystals were dried to obtain 5-chloro-1-(4-methoxyphenyl)-2-oxo-1,2-dihydroquinoxaline-3-carboxylic acid (21.1 g, purity 96.4%, yield 61.4%) as the target product.

Example 16

Production of 5-Chloro-1-(4-methoxyphenyl)-2-oxo-1,2-dihydroquinoxaline-3-carboxylic Acid

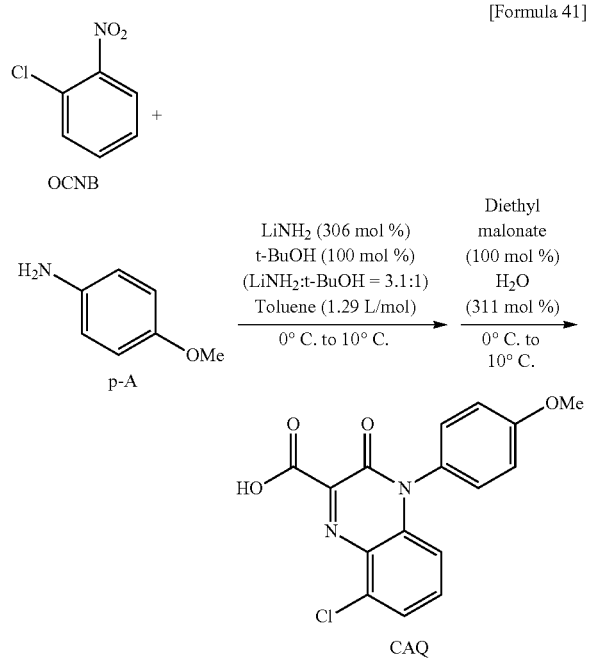

[Formula 41]

Step (i)

Lithium amide (purity: 95.0%, 3.7 g, 153.1 mmol, 306 mol %) was suspended in toluene (28.0 g, 0.65 L/mol) under a nitrogen gas flow. A toluene (11.0 g, 0.25 L/mol) solution of tert-butanol (3.7 g, 49.9 mmol, 100 mol %) was dropped thereinto at an internal temperature of 0 to 10° C. over 30 min, and then the mixture was stirred at the same temperature for 30 min. The internal temperature was maintained at the same temperature, a solution of 2-chloronitrobenzene (7.9 g, 50.1 mmol, 100 mol %) dissolved in toluene (3.0 g, 0.1 L/mol) was added thereto, and then a solution of p-anisidine (6.2 g, 50.0 mmol, 100 mol %) dissolved in toluene (14.0 g, 0.3 L/mol) was dropped over 1 h. The mixture was stirred at the same temperature for 20 h. A reaction mixture including target intermediate 3-chloro-N-(4-methoxyphenyl)-2-nitrosoaniline was obtained.

Step (ii)

The internal temperature was maintained at 0 to 10° C., and water (2.8 g, 155.4 mmol, 311 mol % (based on p-anisidine)) was dropped into the reaction mixture obtained in the above step (i) over 15 min. Then diethyl malonate (8.0 g, 50.0 mmol, 100 mol % (based on p-anisidine)) was dropped at the same temperature over 1 h, and the mixture was stirred at the same temperature for 1 h.

4% hydrochloric acid (94.0 g) was dropped thereinto over 1 h to adjust the pH at 8.3. The internal temperature was increased to 35 to 40° C., water (5.0 g) was added, and then the mixture was divided into toluene and water. The toluene phase was removed. The obtained aqueous phase was washed with toluene (21.8 g×twice), and then 35% hydrochloric acid (10.4 g) was dropped into the aqueous phase at an internal temperature of 20 to 30o over 1 h. The mixture was stirred for 30 min, and then the crystals were filtered. The crystals were sequentially washed with toluene (9.9 g) and water (12.5 g). The obtained crystals were dried to obtain 5-chloro-1-(4-methoxyphenyl)-2-oxo-1,2-dihydroquinoxaline-3-carboxylic acid (11.0 g, purity 95.7%, yield 66.5%) as the target product.

Example 17

Production of 5-Chloro-1-(4-methoxyphenyl)-2-oxo-1,2-dihydroquinoxaline-3-carboxylic Acid

[Formula 42]

Step (i)

Lithium amide (purity: 95.0%, 7.5 g, 310.3 mmol, 311 mol %) was suspended in toluene (20.0 g, 0.23 L/mol) under a nitrogen gas flow. A toluene (4.0 g, 0.05 L/mol) solution of tert-butanol (7.4 g, 99.8 mmol, 100 mol %) was dropped thereinto at an internal temperature of 0 to 10° C. over 30 min, and then the mixture was stirred at the same temperature for 30 min. The internal temperature was maintained at the same temperature, a solution of 2-chloronitrobenzene (23.6 g, 149.8 mmol, 150 mol %) dissolved in toluene (4.0 g, 0.05 L/mol) was added thereto, and then a solution of p-anisidine (12.3 g, 99.9 mmol, 100 mol %) dissolved in toluene (84.4 g, 0.97 L/mol) was dropped over 3 h. The mixture was stirred at the same temperature for 20 h. Then, nitrogen was bubbled into the reaction solution for 8 h to remove ammonia. A reaction mixture including target intermediate 3-chloro-N-(4-methoxyphenyl)-2-nitrosoaniline was obtained.

Step (ii)

The internal temperature was maintained at 0 to 10° C., and water (2.3 g, 149.9 mmol, 150 mol % (based on p-anisidine)) was added to the reaction mixture obtained in the above step (i). Then diethyl malonate (16.0 g, 99.9 mmol, 100 mol % (based on p-anisidine)) was dropped at the same temperature over 1 h, and the mixture was stirred at the same temperature for 7 h. 4% hydrochloric acid was dropped thereinto over 1 h to adjust the pH at 8.1. The internal temperature was increased to 35 to 40° C., water (5.0 g) was added, and then the mixture was divided into toluene and water. The toluene phase was removed. The obtained aqueous phase was washed with toluene (43.5 g×twice), and then 35% hydrochloric acid (20.8 g) was dropped into the aqueous phase at an internal temperature of 20 to 300 over 1 h. The mixture was stirred for 30 min, and then the crystals were filtered. The crystals were sequentially washed with toluene (19.8 g) and water (25.0 g). The obtained crystals were dried to obtain 5-chloro-1-(4-methoxyphenyl)-2-oxo-1,2-dihydroquinoxaline-3-carboxylic acid (25.40 g, purity 98.0%, yield 75.3%) as the target product.

Example 18

Production of 5-Chloro-1-(4-methoxyphenyl)-2-oxo-1,2-dihydroquinoxaline-3-carboxylic Acid

[Formula 43]

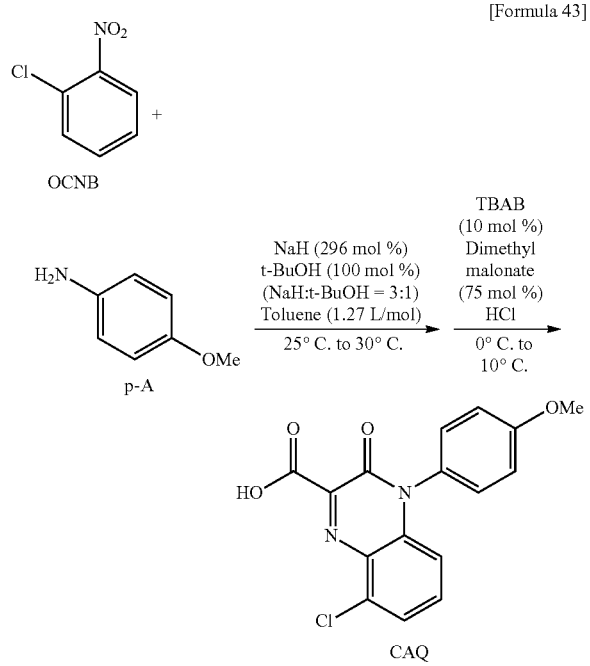

Sodium hydride (purity: 65.1%, liquid paraffin-dispersed, 10.9 g, 295.7 mmol, 296 mol %) was suspended in toluene (56.1 g, 0.65 L/mol) under a nitrogen gas flow. A toluene (27.0 g, 0.31 L/mol) solution of tert-butanol (7.4 g, 99.8 mmol, 100 mol %) was dropped thereinto at an internal temperature of 55 to 60° C. over 30 min, and then the mixture was stirred at the same temperature for 30 min. The internal temperature was cooled to 25 to 30° C., and a solution of 2-chloronitrobenzene (16.5 g, 104.7 mmol, 105 mol %) and p-anisidine (12.3 g, 99.9 mmol, 100 mol %) dissolved in toluene (27.0 g, 0.31 L/mol) was dropped thereinto over 1 h. The mixture was stirred at the same temperature for 2 h. A reaction mixture including target intermediate 3-chloro-N-(4-methoxyphenyl)-2-nitrosoaniline was obtained.

Step (ii)

The internal temperature was cooled to 0° C. to 10° C., and then 35% hydrochloric acid (26.0 g) was dropped until the pH reached 9.7. TBAB (3.2 g, 9.9 mmol, 10 mol % (based on p-anisidine)) and dimethyl malonate (9.9 g, 74.9 mmol, 75 mol % (based on p-anisidine)) were added. The mixture was stirred at the same temperature for 30 min, and then a 48% KOH aqueous solution (4.3 g) was dropped over 2 h until the pH reached 13.3. The mixture was stirred for 2 h, and then a 48% KOH aqueous solution (19.1 g) was dropped over 3 h. The mixture was stirred for 17 h.

4% hydrochloric acid (87.0 g) was dropped at the same temperature over 1 h to adjust the pH at 7.7. The internal temperature was increased to 35 to 40° C., and the mixture was divided into toluene and water. The toluene phase was removed. The obtained aqueous phase was washed with toluene (43.5 g×twice), and then 35% hydrochloric acid (10.4 g) was dropped into the aqueous phase at an internal temperature of 25 to 300 over 2 h. The mixture was stirred for 30 min, and then the crystals were filtered. The crystals were sequentially washed with toluene (19.8 g) and water (25.0 g). The obtained crystals were dried to obtain 5-chloro-1-(4-methoxyphenyl)-2-oxo-1,2-dihydroquinoxaline-3-carboxylic acid (13.9 g, purity 95.2%, yield 39.9%) as the target product.

Example 19

Production of 5-Chloro-1-(4-methoxyphenyl)-2-oxo-1,2-dihydroquinoxaline-3-carboxylic Acid

[Formula 44]

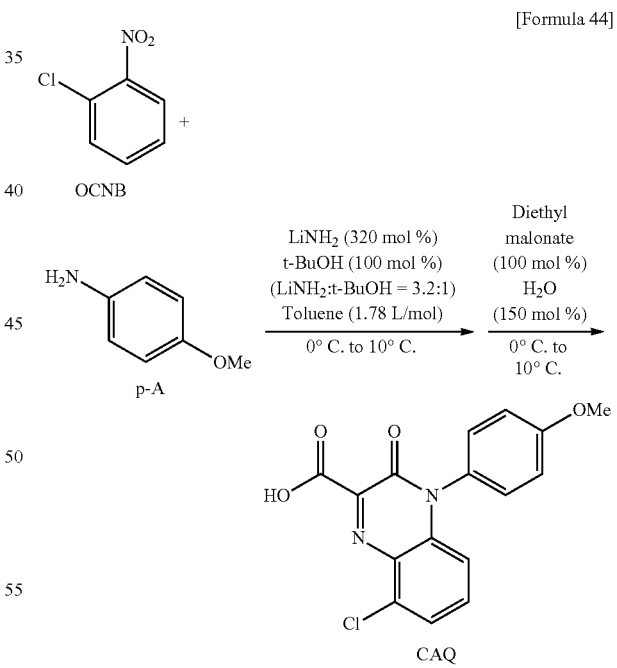

Step (i)

Lithium amide (purity: 98.0%, 7.50 g, 320.1 mmol, 320 mol %) was suspended in toluene (20.0 g, 0.23 L/mol) in a reaction container under a nitrogen gas flow. A toluene (4.0 g, 0.05 L/mol) solution of tert-butanol (7.4 g, 99.8 mmol, 100 mol %) was dropped thereinto at an internal temperature of 0 to 10° C. over 30 min, and then the mixture was stirred at the same temperature for 30 min. The internal temperature was maintained at the same temperature, a solution of 2-chloronitrobenzene (23.6 g, 149.8 mmol, 150 mol %) dissolved in toluene (4.0 g, 0.05 L/mol) was added thereto, and then a solution of p-anisidine (12.3 g, 99.9 mmol, 100 mol %) dissolved in toluene (126.2 g, 1.46 L/mol) was dropped over 3 h. The mixture was stirred at the same temperature for 1 h. A reaction mixture including target intermediate 3-chloro-N-(4-methoxyphenyl)-2-nitrosoaniline was obtained.

Step (ii)

The internal temperature was maintained at 0 to 10° C., and water (2.7 g, 149.8 mmol, 150 mol % (based on p-anisidine)) was dropped into the reaction mixture obtained in the above step (i) over 30 min. After the dropping, ammonia was removed under reduced pressure. Then, diethyl malonate (16.0 g, 99.9 mmol, 100 mol % (based on p-anisidine)) was dropped at the same temperature over 2 h, and the mixture was stirred at the same temperature for 1 h (the end point was determined by analysis).

A mixed solution of tert-butanol (7.4 g, 99.8 mmol, 100 mol %) and water (75 mL, 0.8 L/mol) was added to another reaction container, and the internal temperature was cooled to 0 to 10° C. The previously reacted reaction mixture and 35% hydrochloric acid (23.7 g) were simultaneously dropped thereinto over 30 min to adjust the pH at 7.8. The internal temperature was increased to 25 to 30° C., and 35% hydrochloric acid (20.8 g) was dropped in about 1 h. The mixture was stirred at the same temperature for 30 min, and then the crystals were filtered. The crystals were sequentially washed with toluene (39.6 g) and water (25.0 g). The obtained crystals were dried to obtain 5-chloro-1-(4-methoxyphenyl)-2-oxo-1,2-dihydroquinoxaline-3-carboxylic acid (24.37 g, purity 99.33%, yield 73.2%) as the target product.

According to Examples 15 to 19, the target quinoxaline compound of the formula (5) can be obtained without requiring extreme low temperature. In addition, according to Examples 15 to 19, the amount of the aniline compound, a raw material, used can be reduced.

Example 20

Production of 3-Chloro-N-(4-methoxyphenyl)-2-nitrosoaniline

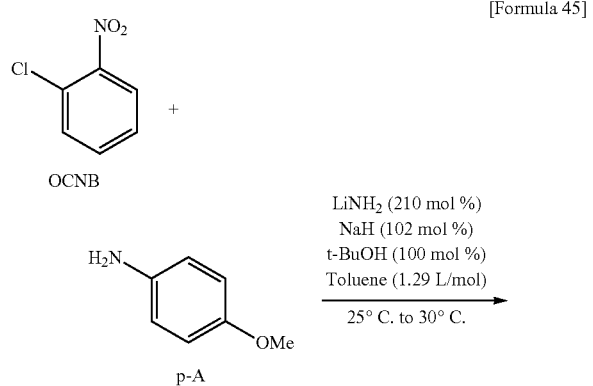

[Formula 45]

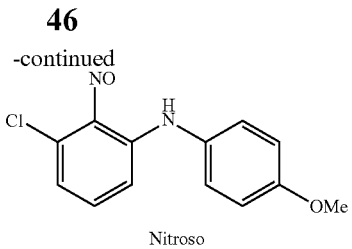

Nitroso

Lithium amide (purity: 95.0%, 2.54 g, 105.1 mmol, 210 mol %) and sodium hydride (purity: 66.3%, liquid paraffin-dispersed, 1.85 g, 51.1 mmol, 102 mol %) were suspended in toluene (10.0 g, 0.23 L/mol) under a nitrogen gas flow. A toluene (2.0 g, 0.05 L/mol) solution of tert-butanol (3.71 g, 50.1 mmol, 100 mol %) was dropped thereinto at an internal temperature of 0 to 10° C. over 30 min, and the mixture was stirred at the same temperature for 30 min. The internal temperature was maintained at the same temperature, a solution of 2-chloronitrobenzene (11.8 g, 74.9 mmol, 150 mol %) dissolved in toluene (2.0 g, 0.05 L/mol) was added thereto, and then the internal temperature was increased to 25° C. to 30° C. The internal temperature was maintained at the same temperature, and a solution of p-anisidine (6.16 g, 50.0 mmol, 100 mol %) dissolved in toluene (42.1 g, 0.97 L/mol) was dropped over 3 h. The mixture was stirred at the same temperature for 1 h.

As a result of the HPLC analysis (area percentage; 254 nm) of the reaction mixture, the main components in the reaction mixture excluding the solvent and the like were as follows;

3-chloro-N-(4-methoxyphenyl)-2-nitrosoaniline (target product): 68.2%,

OCNB (raw material): 14.8%, p-anisidine (raw material): 0.1%,

MNA (by-product; compound by substitution of Cl (compound by elimination of Cl)): 8.7%, CMNA (by-product; nitro derivative corresponding of target product): 2.1%.

The reaction mixture was analyzed by the HPLC absolute calibration curve method to obtain the yield and the like. The results of the analysis were as follows;

3-chloro-N-(4-methoxyphenyl)-2-nitrosoaniline (target product): 81.0% (yield),

OCNB (raw material): 45.9% (recovery rate),

MNA (by-product; compound by substitution of Cl (compound by elimination of Cl)): 6.9%.

Example 21

Production of 3-Chloro-N-(4-methoxyphenyl)-2-nitrosoaniline

[Formula 46]

-continued

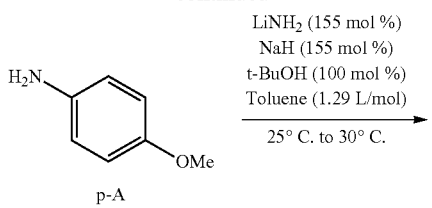

Lithium amide (purity: 95.0%, 1.87 g, 77.4 mmol, 155 mol %) and sodium hydride (purity: 66.3%, liquid paraffin-dispersed, 2.81 g, 77.6 mmol, 155 mol %) were suspended in toluene (10.0 g, 0.23 L/mol) under a nitrogen gas flow. A toluene (2.0 g, 0.05 L/mol) solution of tert-butanol (3.71 g, 50.1 mmol, 100 mol %) was dropped thereinto at an internal temperature of 0 to 10° C. over 30 min, and the mixture was stirred at the same temperature for 30 min. The internal temperature was maintained at the same temperature, a solution of 2-chloronitrobenzene (11.8 g, 74.9 mmol, 150 mol %) dissolved in toluene (2.0 g, 0.05 L/mol) was added thereto, and then the internal temperature was increased to 25° C. to 30° C. The internal temperature was maintained at the same temperature, and a solution of p-anisidine (6.16 g, 50.0 mmol, 100 mol %) dissolved in toluene (42.1 g, 0.97 L/mol) was dropped over 3 h. The mixture was stirred at the same temperature for 1 h.

As a result of the HPLC analysis (area percentage; 254 nm) of the reaction mixture, the main components in the reaction mixture excluding the solvent and the like were as follows;

3-chloro-N-(4-methoxyphenyl)-2-nitrosoaniline (target product): 51.0%,

OCNB (raw material): 13.2%, p-anisidine (raw material): 0.2%,

MNA (by-product; compound by substitution of Cl (compound by elimination of Cl)): 23.0%, CMNA (by-product; nitro derivative corresponding of target product): 3.5%.

The reaction mixture was analyzed by the HPLC absolute calibration curve method to obtain the yield and the like. The results of the analysis were as follows;

3-chloro-N-(4-methoxyphenyl)-2-nitrosoaniline (target product): 57.9% (yield),

OCNB (raw material): 45.4% (recovery rate),

MNA (by-product; compound by substitution of Cl (compound by elimination of Cl)): 20.0%.

Example 22

Production of 3-Chloro-N-(4-methoxyphenyl)-2-nitrosoaniline

[Formula 47]

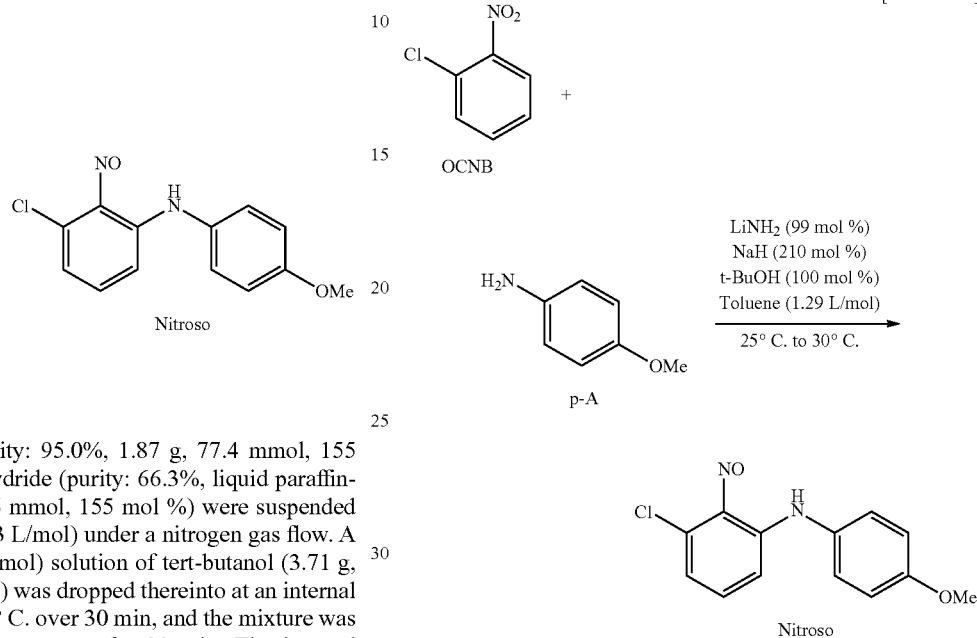

Lithium amide (purity: 95.0%, 1.2 g, 49.7 mmol, 99 mol %) and sodium hydride (purity: 66.3%, liquid paraffin-dispersed, 3.8 g, 105.0 mmol, 210 mol %) were suspended in toluene (10.0 g, 0.23 L/mol) under a nitrogen gas flow. A toluene (2.0 g, 0.05 L/mol) solution of tert-butanol (3.71 g, 50.1 mmol, 100 mol %) was dropped thereinto at an internal temperature of 0 to 10° C. over 30 min, and the mixture was stirred at the same temperature for 30 min. The internal temperature was maintained at the same temperature, a solution of 2-chloronitrobenzene (11.8 g, 74.9 mmol, 150 mol %) dissolved in toluene (2.0 g, 0.05 L/mol) was added thereto, and then the internal temperature was increased to 25° C. to 30° C. The internal temperature was maintained at the same temperature, and a solution of p-anisidine (6.16 g, 50.0 mmol, 100 mol %) dissolved in toluene (42.1 g, 0.97 L/mol) was dropped over 3 h. The mixture was stirred at the same temperature for 1 h.

As a result of the HPLC analysis (area percentage; 254 nm) of the reaction mixture, the main components in the reaction mixture excluding the solvent and the like were as follows;

3-chloro-N-(4-methoxyphenyl)-2-nitrosoaniline (target product): 42.8%,

OCNB (raw material): 12.2%, p-anisidine (raw material): 0.3%,

MNA (by-product; compound by substitution of Cl (compound by elimination of Cl)): 28.1%, CMNA (by-product; nitro derivative corresponding of target product): 5.4%.

The reaction mixture was analyzed by the HPLC absolute calibration curve method to obtain the yield and the like. The results of the analysis were as follows;

3-chloro-N-(4-methoxyphenyl)-2-nitrosoaniline (target product): 51.7% (yield),

OCNB (raw material): 44.8% (recovery rate),

MNA (by-product; compound by substitution of Cl (compound by elimination of Cl)): 26.0%.

Example 23

Production of
3-Chloro-N-(4-methoxyphenyl)-2-nitrosoaniline

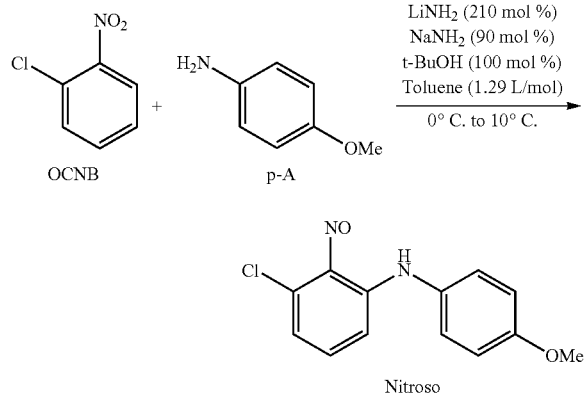

Lithium amide (purity: 98.0%, 2.46 g, 105.0 mmol, 210 mol %) was suspended in toluene (10.0 g, 0.23 L/mol) under a nitrogen gas flow. A toluene (2.0 g, 0.05 L/mol) solution of tert-butanol (3.71 g, 50.1 mmol, 100 mol %) was dropped thereinto at an internal temperature of 0 to 10° C. over 30 min, and the mixture was stirred at the same temperature for 30 min. The internal temperature was maintained at the same temperature, and a solution of 2-chloronitrobenzene (11.8 g, 74.9 mmol, 150 mol %) dissolved in toluene (2.0 g, 0.05 L/mol) was added thereto. Then sodium amide (purity: 90.0%, 1.95 g, 45.0 mmol, 90 mol %) was added, and a solution of p-anisidine (6.16 g, 50.0 mmol, 100 mol %) dissolved in toluene (42.0 g, 0.97 L/mol) was dropped over 4 h. The mixture was stirred at the same temperature for 17 h.

As a result of the HPLC analysis (area percentage; 254 nm) of the reaction mixture, the main components in the reaction mixture excluding the solvent and the like were as follows;

3-chloro-N-(4-methoxyphenyl)-2-nitrosoaniline (target product): 53.9%,

OCNB (raw material): 14.2%, p-anisidine (raw material): 0.2%,

MNA (by-product; compound by substitution of Cl (compound by elimination of Cl)): 18.8%, CMNA (by-product; nitro derivative corresponding of target product): 3.5%.

The reaction mixture was analyzed by the HPLC absolute calibration curve method to obtain the yield and the like. The results of the analysis were as follows;

3-chloro-N-(4-methoxyphenyl)-2-nitrosoaniline (target product): 61.6% (yield),

OCNB (raw material): 48.1% (recovery rate),

MNA (by-product; compound by substitution of Cl (compound by elimination of Cl)): 16.2%.

Example 24

Production of
3-Chloro-N-(4-methoxyphenyl)-2-nitrosoaniline

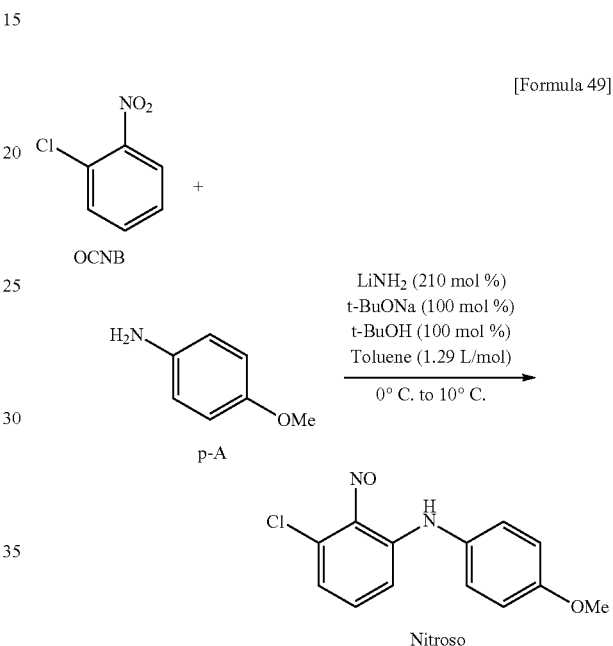

Lithium amide (purity: 98.0%, 2.46 g, 105.0 mmol, 210 mol %) was suspended in toluene (10.0 g, 0.23 L/mol) under a nitrogen gas flow. A toluene (2.0 g, 0.05 L/mol) solution of tert-butanol (3.71 g, 50.1 mmol, 100 mol %) was dropped thereinto at an internal temperature of 0 to 10° C. over 30 min, and the mixture was stirred at the same temperature for 30 min. The internal temperature was maintained at the same temperature, and a solution of 2-chloronitrobenzene (11.8 g, 75.0 mmol, 150 mol %) dissolved in toluene (2.0 g, 0.05 L/mol) was added thereto. Then sodium tert-butoxide (purity: 98.0%, 4.91 g, 50.1 mmol, 100 mol %) was added, and a solution of p-anisidine (6.16 g, 50.0 mmol, 100 mol %) dissolved in toluene (42.0 g, 0.97 L/mol) was dropped over 4 h. The mixture was stirred at the same temperature for 17 h.

As a result of the HPLC analysis (area percentage; 254 nm) of the reaction mixture, the main components in the reaction mixture excluding the solvent and the like were as follows;

3-chloro-N-(4-methoxyphenyl)-2-nitrosoaniline (target product): 47.5%,

OCNB (raw material): 21.8%, p-anisidine (raw material): 0.1%,

MNA (by-product; compound by substitution of CA (compound by elimination of Cl)): 18.7%, CMNA (by-product; nitro derivative corresponding of target product): 1.9%.

The reaction mixture was analyzed by the HPLC absolute calibration curve method to obtain the yield and the like. The results of the analysis were as follows;
3-chloro-N-(4-methoxyphenyl)-2-nitrosoaniline (target product): 54.9% (yield),
OCNB (raw material): 70.4% (recovery rate),
MNA (by-product; compound by substitution of Cl (compound by elimination of Cl)): 15.2%.

Example 25

Production of 3-Chloro-N-(4-methoxyphenyl)-2-nitrosoaniline

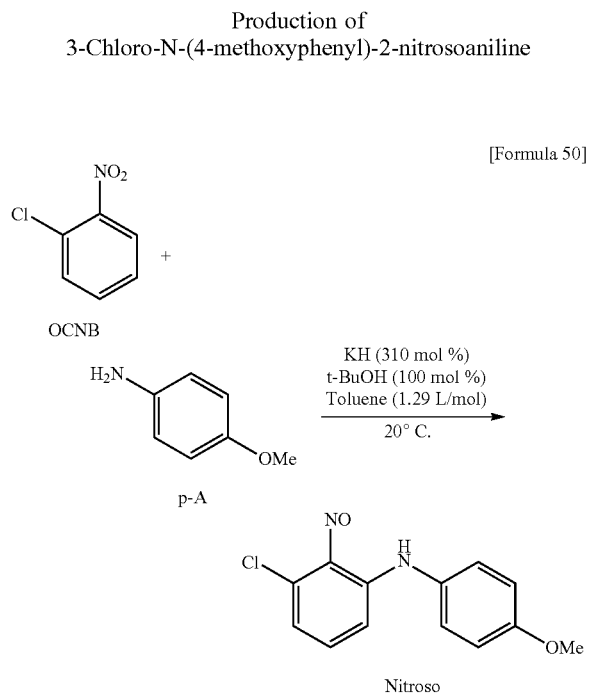

[Formula 50]

Nitroso

Potassium hydride (purity: 30.0%, 20.72 g, 155.0 mmol, 310 mol %) was suspended in toluene (10.0 g, 0.23 L/mol) under a nitrogen gas flow. A toluene (2.0 g, 0.05 L/mol) solution of tert-butanol (3.71 g, 50.1 mmol, 100 mol %) was dropped thereinto at an internal temperature of 0 to 10° C. over 30 min, and then the mixture was stirred at the same temperature for 30 min. The internal temperature was maintained at the same temperature, and a solution of 2-chloronitrobenzene (11.82 g, 75.0 mmol, 150 mol %) dissolved in toluene (2.0 g, 0.05 L/mol) was added thereto. The internal temperature was increased to 20° C., and a solution of p-anisidine (6.16 g, 50.0 mmol, 100 mol %) dissolved in toluene (42.0 g, 0.97 L/mol) was dropped over 3 h. The mixture was stirred at the same temperature for 20 h.

As a result of the HPLC analysis (area percentage; 254 nm) of the reaction mixture, the main components in the reaction mixture excluding the solvent and the like were as follows;
3-chloro-N-(4-methoxyphenyl)-2-nitrosoaniline (target product): 42.6%,
OCNB (raw material): 11.3%,
p-anisidine (raw material): N. D,
MNA (by-product; compound by substitution of Cl (compound by elimination of Cl)): 28.3%,
CMNA (by-product; nitro derivative corresponding of target product): 6.7%.

The reaction mixture was analyzed by the HPLC absolute calibration curve method to obtain the yield and the like. The results of the analysis were as follows;
3-chloro-N-(4-methoxyphenyl)-2-nitrosoaniline (target product): 52.0% (yield),
OCNB (raw material): 41.7% (recovery rate),
MNA (by-product; compound by substitution of Cl (compound by elimination of Cl)): 26.4%.

Example 26

Production of 3-Chloro-N-(4-methoxyphenyl)-2-nitrosoaniline

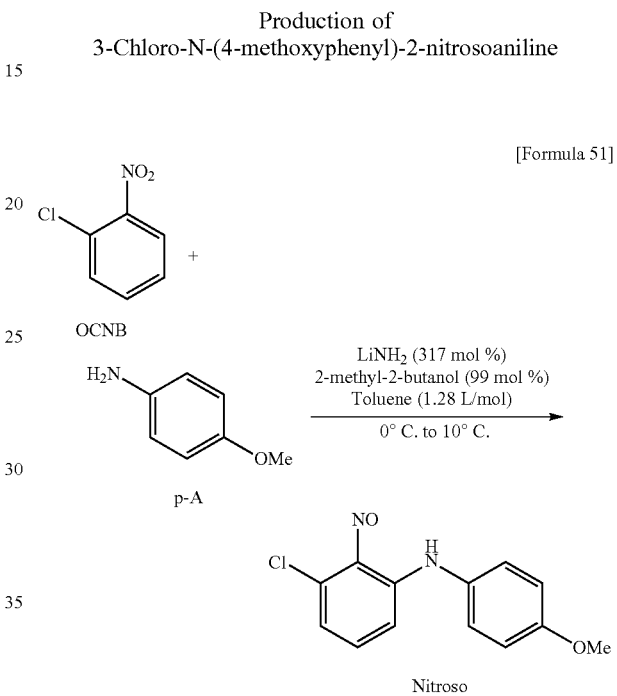

[Formula 51]

Nitroso

Lithium amide (purity: 99.0%, 3.7 g, 160.0 mmol, 317 mol %) was suspended in toluene (10.0 g, 0.23 L/mol) under a nitrogen gas flow. A toluene (2.0 g, 0.05 L/mol) solution of 2-methyl-2-butanol (4.4 g, 49.9 mmol, 99 mol %) was dropped thereinto at an internal temperature of 0 to 10° C. over 30 min, and the mixture was stirred at the same temperature for 30 min. The internal temperature was maintained at the same temperature, a solution of 2-chloronitrobenzene (7.9 g, 50.1 mmol, 100 mol %) dissolved in toluene (2.0 g, 0.05 L/mol) was added thereto, and then a solution of p-anisidine (6.2 g, 50.3 mmol, 100 mol %) dissolved in toluene (42.0 g, 0.96 L/mol) was dropped over 3 h. The mixture was stirred at the same temperature for 20 h.

As a result of the HPLC analysis (area percentage; 254 nm) of the reaction mixture, the main components in the reaction mixture excluding the solvent and the like were as follows;
3-chloro-N-(4-methoxyphenyl)-2-nitrosoaniline (target product): 78.2%,
OCNB (raw material): 0.2%,
p-anisidine (raw material): 0.1%
MNA (by-product; compound by substitution of Cl (compound by elimination of Cl)): 4.1%,
CMNA (by-product; nitro derivative corresponding of target product): 1.7%.

The reaction mixture was analyzed by the HPLC absolute calibration curve method to obtain the yield and the like. The results of the analysis were as follows;
3-chloro-N-(4-methoxyphenyl)-2-nitrosoaniline (target product): 74.0% (yield),
OCNB (raw material): trace,
MNA (by-product; compound by substitution of Cl (compound by elimination of Cl)): 3.0%.

Example 27

Production of
3-Chloro-N-(4-methoxyphenyl)-2-nitrosoaniline

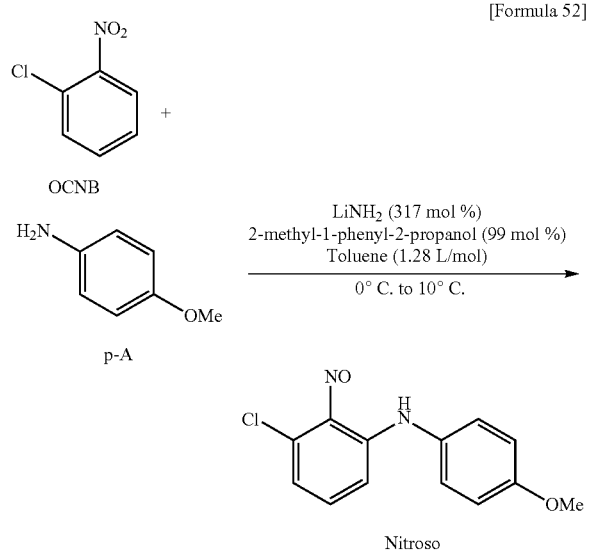

[Formula 52]

Lithium amide (purity: 99.0%, 3.7 g, 160.0 mmol, 317 mol %) was suspended in toluene (10.0 g, 0.23 L/mol) under a nitrogen gas flow. A toluene (2.0 g, 0.05 L/mol) solution of 2-methyl-1-phenyl-2-propanol (7.5 g, 49.9 mmol, 99 mol %) was dropped thereinto at an internal temperature of 0 to 10° C. over 30 min, and the mixture was stirred at the same temperature for 30 min. The internal temperature was maintained at the same temperature, a solution of 2-chloronitrobenzene (7.9 g, 50.1 mmol, 100 mol %) dissolved in toluene (2.0 g, 0.05 L/mol) was added thereto, and then a solution of p-anisidine (6.2 g, 50.3 mmol, 100 mol %) dissolved in toluene (42.0 g, 0.96 L/mol) was dropped over 3 h. The mixture was stirred at the same temperature for 20 h.

As a result of the HPLC analysis (area percentage; 254 nm) of the reaction mixture, the main components in the reaction mixture excluding the solvent and the like were as follows;
3-chloro-N-(4-methoxyphenyl)-2-nitrosoaniline (target product): 66.8%,
OCNB (raw material): 0.4%,
p-anisidine (raw material): 0.1%
MNA (by-product; compound by substitution of Cl (compound by elimination of Cl)): 7.9%,
CMNA (by-product; nitro derivative corresponding of target product): 0.3%.

The reaction mixture was analyzed by the HPLC absolute calibration curve method to obtain the yield and the like. The results of the analysis were as follows;
3-chloro-N-(4-methoxyphenyl)-2-nitrosoaniline (target product): 65.7% (yield),
OCNB (raw material): 1.3% (recovery rate),
MNA (by-product; compound by substitution of Cl (compound by elimination of Cl)): 5.9%.

Example 28

Production of
3-Chloro-N-(4-methoxyphenyl)-2-nitrosoaniline

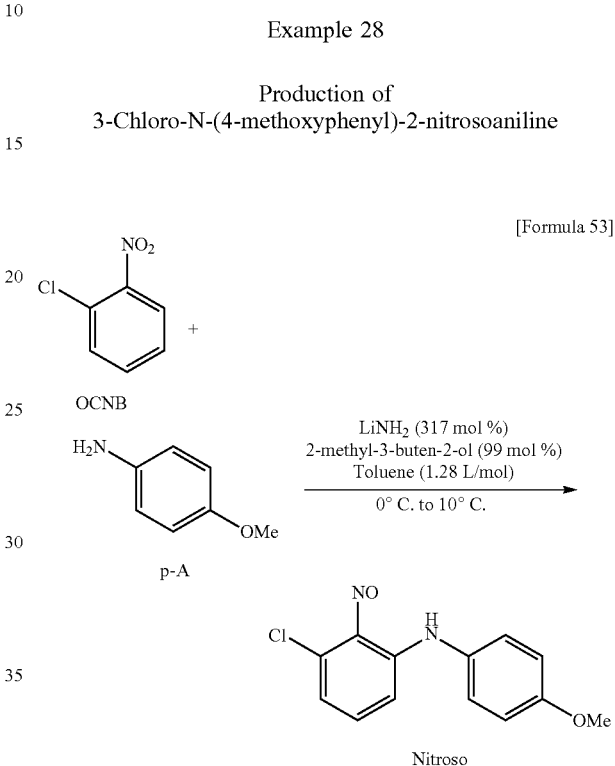

[Formula 53]

Lithium amide (purity: 99.0%, 3.7 g, 160.0 mmol, 317 mol %) was suspended in toluene (10.0 g, 0.23 L/mol) under a nitrogen gas flow. A toluene (2.0 g, 0.05 L/mol) solution of 2-methyl-3-buten-2-ol (4.3 g, 49.9 mmol, 99 mol %) was dropped thereinto at an internal temperature of 0 to 10° C. over 30 min, and the mixture was stirred at the same temperature for 30 min. The internal temperature was maintained at the same temperature, a solution of 2-chloronitrobenzene (7.9 g, 50.1 mmol, 100 mol %) dissolved in toluene (2.0 g, 0.05 L/mol) was added thereto, and then a solution of p-anisidine (6.2 g, 50.3 mmol, 100 mol %) dissolved in toluene (42.0 g, 0.96 L/mol) was dropped over 3 h. The mixture was stirred at the same temperature for 20 h.

As a result of the HPLC analysis (area percentage; 254 nm) of the reaction mixture, the main components in the reaction mixture excluding the solvent and the like were as follows;
3-chloro-N-(4-methoxyphenyl)-2-nitrosoaniline (target product): 71.9%,
OCNB (raw material): 2.5%,
p-anisidine (raw material): 0.1%,
MNA (by-product; compound by substitution of Cl (compound by elimination of Cl)): 5.8%,
CMNA (by-product; nitro derivative corresponding of target product): 1.8%.

The reaction mixture was analyzed by the HPLC absolute calibration curve method to obtain the yield and the like. The results of the analysis were as follows;

3-chloro-N-(4-methoxyphenyl)-2-nitrosoaniline (target product): 78.8% (yield),

OCNB (raw material): 3.0% (recovery rate),

MNA (by-product; compound by substitution of Cl (compound by elimination of Cl)): 4.8%.

Example 29

Production of 3-Chloro-N-(4-methoxyphenyl)-2-nitrosoaniline (2-Methyl-3-phenyl-1-propanol)

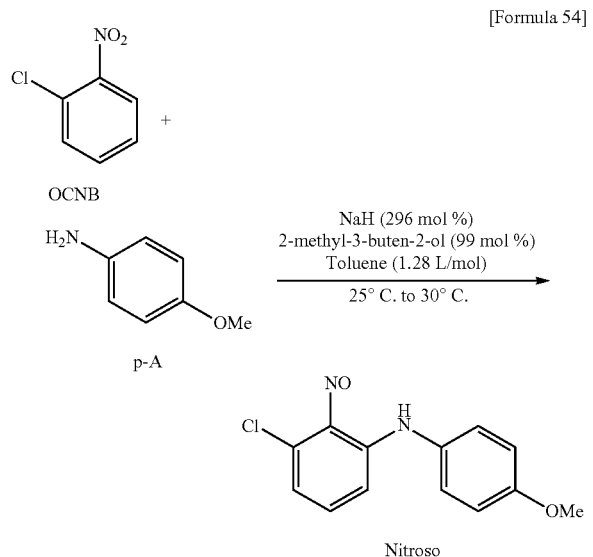

[Formula 54]

Nitroso

Sodium hydride (purity: 66.3%, liquid paraffin-dispersed, 5.4 g, 149.2 mmol, 296 mol %) was suspended in toluene (28.0 g, 0.64 L/mol) under a nitrogen gas flow. A toluene (14.0 g, 0.32 L/mol) solution of 2-methyl-3-buten-2-ol (4.3 g, 49.9 mmol, 99 mol %) was dropped thereinto at an internal temperature of 55 to 60° C. over 30 min, and the mixture was stirred at the same temperature for 30 min. The internal temperature was cooled to 25 to 30° C., and a solution of p-anisidine (6.2 g, 50.3 mmol, 100 mol %) and 2-chloronitrobenzene (7.9 g, 50.1 mmol, 100 mol %) dissolved in toluene (14.0 g, 0.32 L/mol) was dropped thereinto over 1 h. The mixture was stirred at the same temperature for 20 h.

As a result of the HPLC analysis (area percentage; 254 nm) of the reaction mixture, the main components in the reaction mixture excluding the solvent and the like were as follows;

3-chloro-N-(4-methoxyphenyl)-2-nitrosoaniline (target product): 55.0%,

OCNB (raw material): 2.5%, p-anisidine (raw material): 0.4%

MNA (by-product; compound by substitution of Cl (compound by elimination of Cl)): 28.8%, CMNA (by-product; nitro derivative corresponding of target product): 3.5%.

The reaction mixture was analyzed by the HPLC absolute calibration curve method to obtain the yield and the like. The results of the analysis were as follows;

3-chloro-N-(4-methoxyphenyl)-2-nitrosoaniline (target product): 45.0% (yield),

OCNB (raw material): 6.2% (recovery rate),

MNA (by-product; compound by substitution of Cl (compound by elimination of Cl)): 18.0%.

Example 30

Production of 3-Chloro-2-nitroso-N-phenylaniline

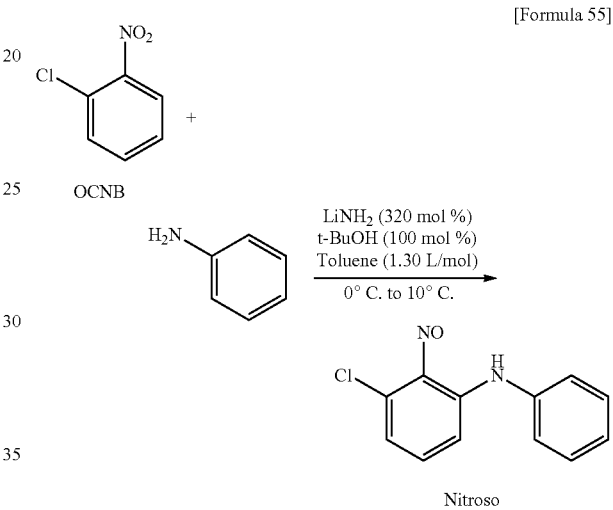

[Formula 55]

Nitroso

Lithium amide (purity: 99.0%, 3.7 g, 160.0 mmol, 320 mol %) was suspended in toluene (10.0 g, 0.23 L/mol) under a nitrogen gas flow. A toluene (2.0 g, 0.05 L/mol) solution of tert-butanol (3.71 g, 50.1 mmol, 100 mol %) was dropped thereinto at an internal temperature of 0 to 10° C. over 30 min, and then the mixture was stirred at the same temperature for 30 min. The internal temperature was maintained at the same temperature, a solution of 2-chloronitrobenzene (7.9 g, 50.1 mmol, 100 mol %) dissolved in toluene (2.0 g, 0.05 L/mol) was added thereto, and then a solution of aniline (4.65 g, 49.9 mmol, 100 mol %) dissolved in toluene (42.1 g, 0.97 L/mol) was dropped over 30 min. The mixture was stirred at the same temperature for 20 h.

As a result of the HPLC analysis (area percentage; 254 nm) of the reaction mixture, the main components in the reaction mixture excluding the solvent and the like were as follows;

3-chloro-2-nitroso-N-phenylaniline (target product): 89.5%, aniline (raw material): N. D, OCNB (raw material): 1.6%.

The reaction mixture was analyzed by the HPLC absolute calibration curve method to obtain the yield and the like. The results of the analysis were as follows;

3-chloro-2-nitroso-N-phenylaniline (target product): 91.5% (yield),

OCNB (raw material): 5.0% (recovery rate).

Example 31

Production of 3-Chloro-2-nitroso-N-phenylaniline

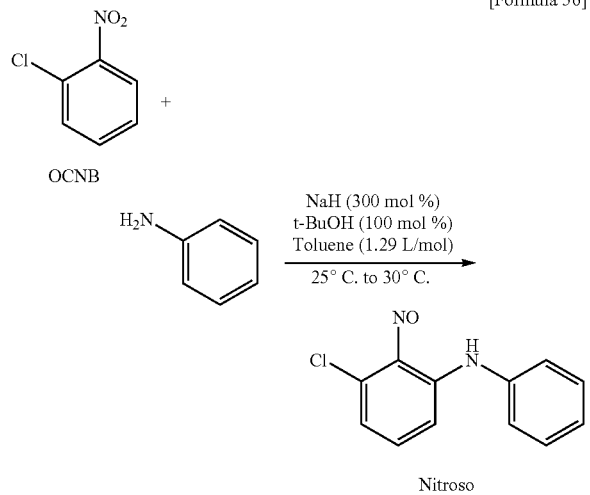

[Formula 56]

Sodium hydride (purity: 66.3%, liquid paraffin-dispersed, 5.44 g, 150.3 mmol, 300 mol %) was suspended in toluene (28.0 g, 0.65 L/mol) under a nitrogen gas flow. A toluene (14.0 g, 0.32 L/mol) solution of tert-butanol (3.71 g, 50.1 mmol, 100 mol %) was dropped thereinto at an internal temperature of 55 to 60° C. over 30 min, and then the mixture was stirred at the same temperature for 30 min. The internal temperature was cooled to 25 to 30° C., and a solution of aniline (4.66 g, 50.0 mmol, 100 mol %) and 2-chloronitrobenzene (7.9 g, 50.1 mmol, 100 mol %) dissolved in toluene (14.0 g, 0.32 L/mol) was dropped thereinto over 1 h. The mixture was stirred at the same temperature for 20 h.

As a result of the HPLC analysis (area percentage; 254 nm) of the reaction mixture, the main components in the reaction mixture excluding the solvent and the like were as follows;
3-chloro-2-nitroso-N-phenylaniline (target product): 54.9%,
OCNB (raw material): 2.2%,
aniline (raw material): N. D.

The reaction mixture was analyzed by the HPLC absolute calibration curve method to obtain the yield and the like. The results of the analysis were as follows;
3-chloro-2-nitroso-N-phenylaniline (target product): 55.0% (yield),
OCNB (raw material): 6.8% (recovery rate).

According to Examples 20 to 31, the target nitroso compound can be obtained without requiring extreme low temperature. In addition, according to Examples 20 to 31, the amount of the aniline compound, a raw material, used can be reduced.

Comparative Example 1

A reaction and analysis were performed in the same manner as Example 1 except that tert-butanol (t-BuOH) was not used.

As a result of the HPLC analysis (area percentage; 254 nm) of the reaction mixture, the main components in the reaction mixture excluding the solvent and the like were as follows;
3-chloro-N-(4-methoxyphenyl)-2-nitrosoaniline (target product): 0.5%,
OCNB (raw material): 82.6%,
p-anisidine (raw material): 11.6%,
MNA (by-product; compound by substitution of Cl (compound by elimination of Cl)): 2.7%,
CMNA (by-product; nitro derivative corresponding of target product): 0.3%.

The reaction mixture was analyzed by the HPLC absolute calibration curve method to obtain the yield and the like. The results of the analysis were as follows;
3-chloro-N-(4-methoxyphenyl)-2-nitrosoaniline (target product): trace (yield),
OCNB (raw material): 94.6% (recovery rate),
MNA (by-product; compound by substitution of Cl (compound by elimination of Cl)): trace.

Comparative Example 2

A reaction and analysis were performed in the same manner as Example 5 except that t-BuOH was not used.

As a result of the HPLC analysis (area percentage; 254 nm) of the reaction mixture, the main components in the reaction mixture excluding the solvent and the like were as follows;
3-chloro-N-(4-methoxyphenyl)-2-nitrosoaniline (target product): N. D,
OCNB (raw material): 87.4%,
p-anisidine (raw material): 12.6%,
MNA (by-product; compound by substitution of Cl (compound by elimination of Cl)): N. D,
CMNA (by-product; nitro derivative corresponding of target product): N. D.

The reaction mixture was analyzed by the HPLC absolute calibration curve method to obtain the yield and the like. The results of the analysis were as follows;
3-chloro-N-(4-methoxyphenyl)-2-nitrosoaniline (target product): N. D (yield),
OCNB (raw material): 100% (recovery rate),
MNA (by-product; compound by substitution of CA (compound by elimination of Cl)): N. D.

Comparative Example 3

Production of 3-Chloro-N-(4-methoxyphenyl)-2-nitrosoaniline

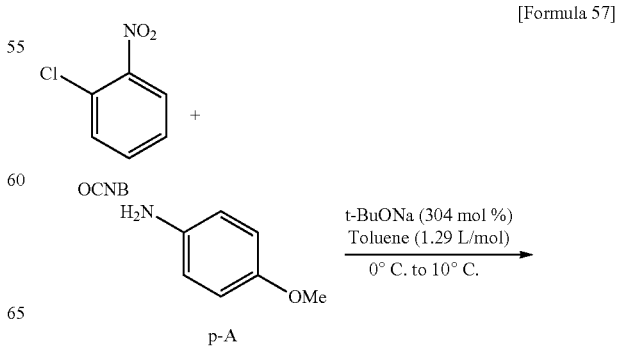

[Formula 57]

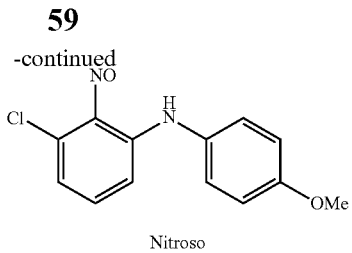

Nitroso

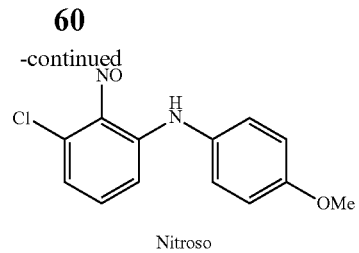

Nitroso tert-Butoxysodium (purity: 98.0%, 5.96 g, 60.8 mmol, 304 mol %) was suspended in toluene (16.8 g, 0.97 L/mol) under a nitrogen gas flow. The suspension was stirred at an internal temperature of 0 to 10° C. for 30 min. The internal temperature was maintained at the same temperature, and a solution of p-anisidine (2.46 g, 20.0 mmol, 100 mol %) and 2-chloronitrobenzene (3.15 g, 20.0 mmol, 100 mol %) dissolved in toluene (5.6 g, 0.32 L/mol) was dropped thereinto over 1 h. The mixture was stirred at the same temperature for 20 h.

As a result of the HPLC analysis (area percentage; 254 nm) of the reaction mixture, the main components in the reaction mixture excluding the solvent and the like were as follows;

3-chloro-N-(4-methoxyphenyl)-2-nitrosoaniline (target product): 36.7%,

OCNB (raw material): 17.6%, p-anisidine (raw material): 2.4%,

MNA (by-product; compound by substitution of Cl (compound by elimination of Cl)): 29.7%, CMNA (by-product; nitro derivative corresponding of target product): 5.7%.

The reaction mixture was analyzed by the HPLC absolute calibration curve method to obtain the yield and the like. The results of the analysis were as follows;

3-chloro-N-(4-methoxyphenyl)-2-nitrosoaniline (target product): 30.6% (yield),

OCNB (raw material): 43.3% (recovery rate),

MNA (by-product; compound by substitution of Cl (compound by elimination of Cl)): 17.0%.

Comparative Example 4

Production of 3-Chloro-N-(4-methoxyphenyl)-2-nitrosoaniline

Under a nitrogen gas flow, tert-butoxylithium (purity: 97.0%, 12.8 g, 155.1 mmol, 308 mol %) was suspended in toluene (42.0 g, 0.96 L/mol), and the suspension was stirred at an internal temperature of 0° C. to 10° C. for 30 min. The internal temperature was maintained at the same temperature, and a solution of p-anisidine (6.2 g, 50.3 mmol, 100 mol %) and 2-chloronitrobenzene (7.9 g, 50.1 mmol, 100 mol %) dissolved in toluene (14.0 g, 0.32 L/mol) was dropped thereinto over 1 h. The mixture was stirred at the same temperature for 20 h. When analysis was performed in the same manner as Example 1, the target nitroso compound had been slightly produced, and most of the unreacted raw materials had remained.

As a result of the HPLC analysis (area percentage; 254 nm) of the reaction mixture, the main components in the reaction mixture excluding the solvent and the like were as follows;

3-chloro-N-(4-methoxyphenyl)-2-nitrosoaniline (target product): 0.6%,

OCNB (raw material): 76.9%, p-anisidine (raw material): 22.0%.

The reaction mixture was analyzed by the HPLC absolute calibration curve method to obtain the yield and the like. The results of the analysis were as follows;

3-chloro-N-(4-methoxyphenyl)-2-nitrosoaniline (target product): trace (yield),

OCNB (raw material): 100.0% (recovery rate).

Comparative Example 5

Method Described in Tetrahedron (2016) 8252-8260 (Non Patent Literature 2)

Production of 3-Chloro-N-(4-methoxyphenyl)-2-nitrosoaniline

[Formula 58]

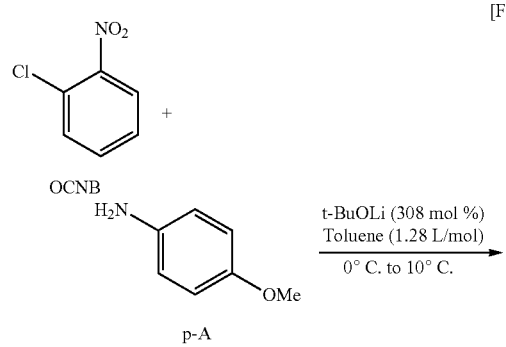

[Formula 59]

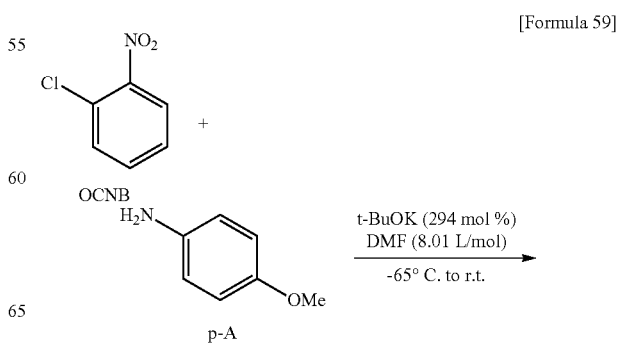

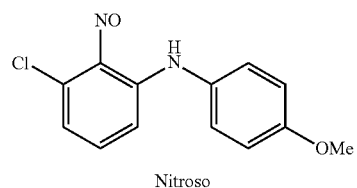

Nitroso

Under a nitrogen gas flow, the internal temperature was cooled to −65° C., and tert-butoxypotassium (purity: 97.0%, 3.4 g, 29.4 mmol, 294 mol %) was suspended in N,N-dimethylformamide (DMF) (60.0 ml, 6.0 L/mol). As a result, the mixture froze. The internal temperature was maintained at the same temperature, a solution of p-anisidine (1.23 g, 10.0 mmol, 100 mol %) dissolved in N,N-dimethylformamide (10.0 ml, 1.0 L/mol) was added thereto, and then a solution of 2-chloronitrobenzene (1.58 g, 10.0 mmol, 100 mol %) dissolved in N,N-dimethylformamide (10.0 ml, 1.0 L/mol) was dropped. The mixture was stirred at the same temperature for 30 min. Then the cooling bath was removed, and the temperature was increased to room temperature over 30 min. The mixture was stirred at room temperature for 50 min, and then the reaction mixture was poured into a saturated ammonium chloride aqueous solution (250.0 ml), followed by extraction with ethyl acetate (100.0 ml). The obtained organic layer was sequentially washed with water (50.0 ml) and a saturated saline solution (50.0 ml) to obtain an ethyl acetate solution including the target product.

As a result of the HPLC analysis (area percentage; 254 nm) of the obtained ethyl acetate solution, the main components were as follows;

3-chloro-N-(4-methoxyphenyl)-2-nitrosoaniline (target product): 29.3%,

OCNB (raw material): 0.7%, p-anisidine (raw material): 0.9%,

MNA (by-product; compound by substitution of Cl (compound by elimination of Cl)): 15.0%, CMNA (by-product; nitro derivative corresponding of target product): 0.1%.

The obtained ethyl acetate solution was analyzed by the HPLC absolute calibration curve method to obtain the yield and the like. The results of the analysis were as follows;

3-chloro-N-(4-methoxyphenyl)-2-nitrosoaniline (target product): 30.5%,

OCNB (raw material): 0.7%,

MNA (by-product; compound by substitution of Cl (compound by elimination of Cl)): 11.3%.

Comparative Example 6

A reaction and post-treatment were carried out in the same manner as the method described in Tetrahedron (2016) 8252-8260 (Non Patent Literature 2) except that the reaction temperature was changed to room temperature.

Production of
3-Chloro-N-(4-methoxyphenyl)-2-nitrosoaniline

[Formula 60]

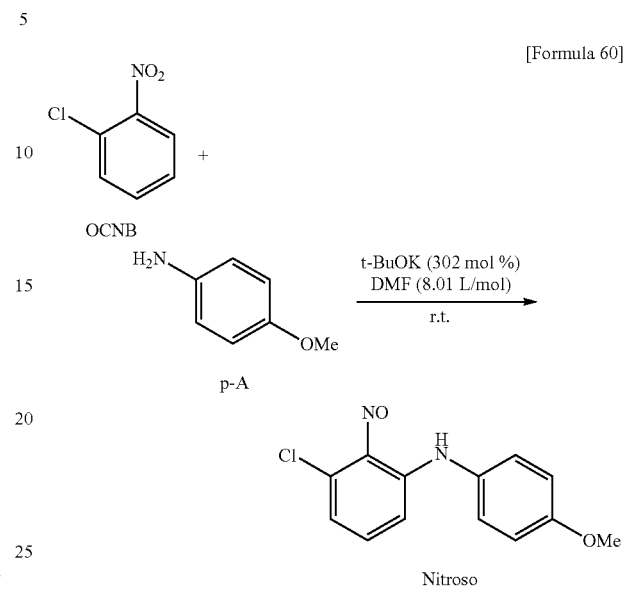

tert-Butoxypotassium (purity: 97.0%, 3.4 g, 29.4 mmol, 302 mol %) was suspended in N,N-dimethylformamide (60.0 ml, 6.01 L/mol) under a nitrogen gas flow. A solution of p-anisidine (1.2 g, 9.7 mmol, 100 mol %) dissolved in N,N-dimethylformamide (10.0 ml, 1.00 L/mol) was added thereto at room temperature, and then a solution of 2-chloronitrobenzene (1.5 g, 9.5 mmol, 98 mol %) dissolved in N,N-dimethylformamide (10.0 ml, 1.00 L/mol) was dropped at room temperature. The mixture was stirred at room temperature for 1 h. The reaction mixture was poured into a saturated ammonium chloride aqueous solution (250.0 ml), followed by extraction with ethyl acetate (100.0 ml). The obtained organic layer was sequentially washed with water (50.0 ml) and a saturated saline solution (50.0 ml) to obtain an ethyl acetate solution including the target product.

As a result of the HPLC analysis (area percentage; 254 nm) of the obtained ethyl acetate solution, the main components were as follows;

3-chloro-N-(4-methoxyphenyl)-2-nitrosoaniline (target product): 7.3%,

OCNB (raw material): 3.6%, p-anisidine (raw material): 1.4%,

MNA (by-product; compound by substitution of Cl (compound by elimination of Cl)): 1.6%, CMNA (by-product; nitro derivative corresponding of target product): 0.1%.

The obtained ethyl acetate solution was analyzed by the HPLC absolute calibration curve method to obtain the yield and the like. The results of the analysis were as follows;

3-chloro-N-(4-methoxyphenyl)-2-nitrosoaniline (target product): 0.5%,

OCNB (raw material): 10.8%,

MNA (by-product; compound by substitution of Cl (compound by elimination of Cl)): 1.2%.

Comparative Example 7

Method Described in Synlett (2015) 1352-1356 (Non Patent Literature 1)

Production of 3-Chloro-N-(4-methoxyphenyl)-2-nitrosoaniline

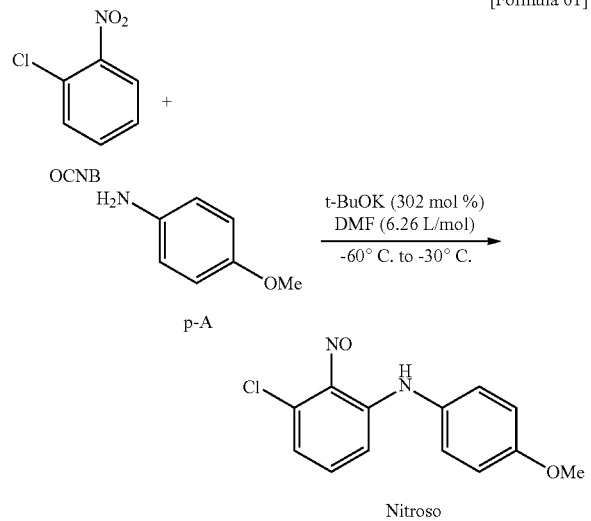

[Formula 61]

Under a nitrogen gas flow, the internal temperature was cooled to −60° C., and tert-butoxypotassium (purity: 97.0%, 3.4 g, 29.4 mmol, 302 mol %) was suspended in N,N-dimethylformamide (50.0 ml, 5.13 L/mol). A solution of p-anisidine (1.2 g, 9.7 mmol, 100 mol %) dissolved in N,N-dimethylformamide (3.0 ml, 0.31 L/mol) was added thereto, and then a solution of 2-chloronitrobenzene (1.5 g, 9.5 mmol, 98 mol %) dissolved in N,N-dimethylformamide (8.0 ml, 0.82 L/mol) was dropped. The internal temperature was maintained at the same temperature, and the mixture was stirred for 30 min. The internal temperature was increased to −30° C., and the mixture was stirred for 1 h. The mixture was poured into a saturated ammonium chloride aqueous solution (250.0 ml), followed by extraction with ethyl acetate (100.0 ml). The obtained organic layer was sequentially washed with water (50.0 ml) and a saturated saline solution (50.0 ml) to obtain an ethyl acetate solution including the target product.

As a result of the HPLC analysis (area percentage; 254 nm) of the obtained ethyl acetate solution, the main components were as follows;
3-chloro-N-(4-methoxyphenyl)-2-nitrosoaniline (target product): 22.2%,
OCNB (raw material): 7.0%,
p-anisidine (raw material): 0.9%,
MNA (by-product; compound by substitution of Cl (compound by elimination of Cl)): 31.1%,
CMNA (by-product; nitro derivative corresponding of target product): 0.2%.

The obtained ethyl acetate solution was analyzed by the HPLC absolute calibration curve method to obtain the yield and the like. The results of the analysis were as follows;
3-chloro-N-(4-methoxyphenyl)-2-nitrosoaniline (target product): 18.2%,
OCNB (raw material): 16.1%,
MNA (by-product; compound by substitution of Cl (compound by elimination of Cl)): 4.2%.

Comparative Example 8

Method Described in Chemistry of Heterocyclic Compounds 2018, 54(9), 875-886 (Non Patent Literature 3)

Production of 3-Chloro-N-(4-methoxyphenyl)-2-nitrosoaniline

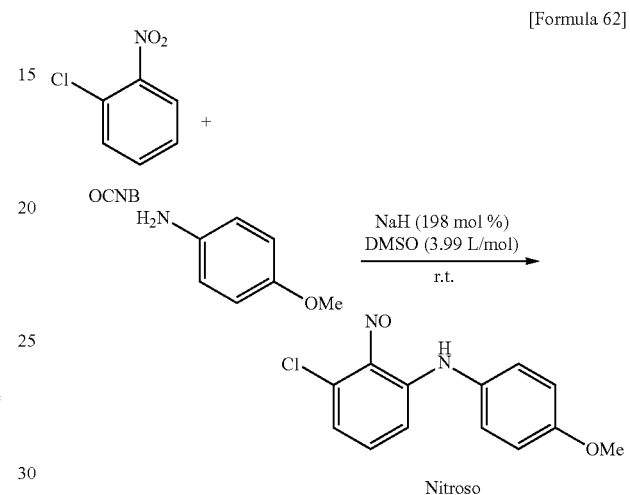

[Formula 62]

p-Anisidine (1.23 g, 10.0 mmol, 199 mol %) was dissolved in dimethyl sulfoxide (DMSO) (20.0 ml, 4.00 L/mol) under a nitrogen gas flow. Sodium hydride (66.3%, liquid paraffin-dispersed, 0.36 g, 9.95 mmol, 198 mol %) was added thereto at room temperature, and then 2-chloronitrobenzene (0.79 g, 5.0 mmol, 100 mol %) was added. The internal temperature was maintained at room temperature, and the mixture was stirred for 1 h. The mixture was poured into a saturated saline solution cooled with ice water, and the precipitated crystals were filtered. The obtained crystals were dissolved in toluene to obtain a toluene solution including the target product.

As a result of the HPLC analysis (area percentage; 254 nm) of the reaction mixture, the main components in the reaction mixture excluding the solvent and the like were as follows;
3-chloro-N-(4-methoxyphenyl)-2-nitrosoaniline (target product): 0.5%,
OCNB (raw material): 27.5%,
p-anisidine (raw material): 1.5%
MNA (by-product; compound by substitution of Cl (compound by elimination of Cl)): 15.5%,
CMNA (by-product; nitro derivative corresponding of target product): 0.3%.

The reaction mixture was analyzed by the HPLC absolute calibration curve method to obtain the yield and the like. The results of the analysis were as follows;
3-chloro-N-(4-methoxyphenyl)-2-nitrosoaniline (target product): 0.8% (yield),
OCNB (raw material): 56.5% (recovery rate),
MNA (by-product; compound by substitution of Cl (compound by elimination of Cl)): 8.0%.

Comparative Example 9

Production of
3-Chloro-N-(4-methoxyphenyl)-2-nitrosoaniline

As described above, in the method of Japanese Patent Laid-Open No. 2018-70520 (Patent Literature 3), the reaction of 2-chloronitrobenzene requires low temperature. In Comparative Example 9, the method of Japanese Patent Laid-Open No. 2018-70520 (Patent Literature 3) was performed with the temperature of the reaction changed to 25 to 30° C. to avoid such low temperature. As a result, a low yield was provided as described below. In the method of Japanese Patent Laid-Open No. 2018-70520 (Patent Literature 3), such low temperature could not be avoided.

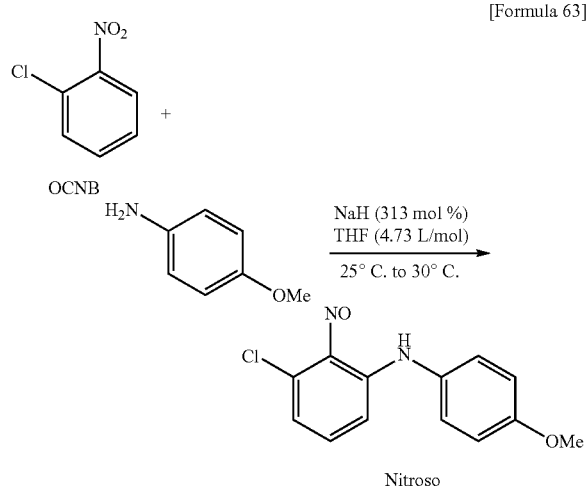

[Formula 63]

Sodium hydride (66.3%, liquid paraffin-dispersed, 0.36 g, 9.95 mmol, 313 mol %) was suspended in THF (5 ml, 1.58 L/mol). Under a nitrogen gas flow, a solution of p-anisidine (1.17 g, 9.50 mmol, 299 mol %) dissolved in THF (5 ml, 1.58 L/mol) was added while the internal temperature was kept at 55 to 60° C., and the mixture was stirred at the same temperature for 2 h. The mixture was cooled to room temperature. Separately, 2-chloronitrobenzene (0.50 g, 3.17 mmol, 100 mol %) was dissolved in THF (5 ml, 1.58 L/mol) under a nitrogen gas flow. The mixture previously prepared using p-anisidine and sodium hydride was added thereto at an internal temperature of 25 to 30° C., and the obtained mixture was stirred at the same temperature for 2 h. The mixture was poured into a saturated ammonium chloride aqueous solution. Then, the mixture was subjected to extraction with ethyl acetate. The obtained organic layer was washed with a saturated saline solution to obtain an ethyl acetate solution including the target product.

As a result of the HPLC analysis (area percentage; 254 nm) of the reaction mixture, the main components in the reaction mixture excluding the solvent and the like were as follows;
3-chloro-N-(4-methoxyphenyl)-2-nitrosoaniline (target product): 23.4%,
OCNB (raw material): 0.9%,
p-anisidine (raw material): N. D
MNA (by-product; compound by substitution of Cl (compound by elimination of Cl)): 34.5%,
CMNA (by-product; nitro derivative corresponding of target product): 2.1%.

The reaction mixture was analyzed by the HPLC absolute calibration curve method to obtain the yield and the like. The results of the analysis were as follows;
3-chloro-N-(4-methoxyphenyl)-2-nitrosoaniline (target product): 31.0% (yield),
OCNB (raw material): 3.8% (recovery rate),
MNA (by-product; compound by substitution of Cl (compound by elimination of Cl)): 34.8%.

Comparative Example 10

Production of
3-Chloro-N-(4-methoxyphenyl)-2-nitrosoaniline

A reaction and analysis were performed in the same manner as Example 5 except that a secondary alcohol (2-propanol, that is, 2-propanol) was used instead of the tertiary alcohol (tert-butanol).

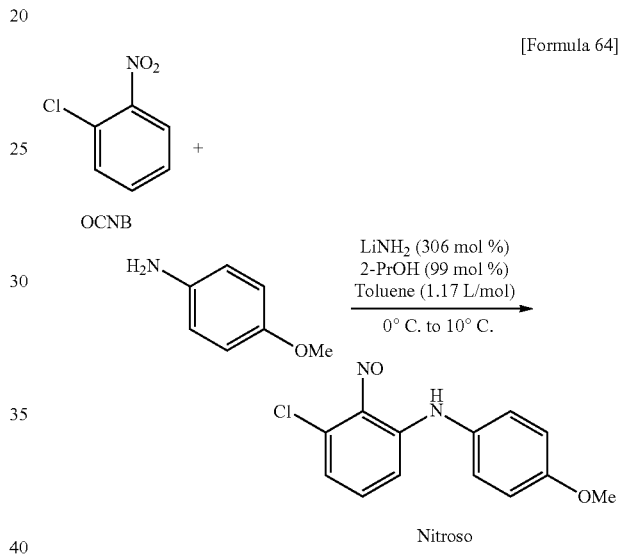

[Formula 64]

Lithium amide (purity: 95.0%, 3.72 g, 153.9 mmol, 306 mol %) was suspended in toluene (10.0 g, 0.23 L/mol) under a nitrogen gas flow. A toluene (2.0 g, 0.05 L/mol) solution of 2-propanol (2.99 g, 49.8 mmol, 99 mol %) was dropped thereinto at an internal temperature of 0 to 10° C. over 30 min, and then the mixture was stirred at the same temperature for 30 min. The internal temperature was maintained at the same temperature, a solution of 2-chloronitrobenzene (7.9 g, 50.1 mmol, 100 mol %) dissolved in toluene (2.0 g, 0.05 L/mol) was added thereto, and then a solution of p-anisidine (6.2 g, 50.3 mmol, 100 mol %) dissolved in toluene (37.0 g, 0.85 L/mol) was dropped. After the dropping, the temperature increased to 50° C. or more, and black smoke was generated. Therefore the reaction was stopped.

As shown in Comparative Examples 1 to 4 and 9 to 10, it is seen that when either one of a tertiary alcohol and a base is not used, the target nitroso compound of the formula (3) cannot be obtained, or a low yield is obtained.

As shown in Comparative Examples 5 to 8, even if the methods of the related art were applied to raw materials having the combination of the substituents of herbicide Fenquinotrione, the reactions did not proceed sufficiently. In sum, it was confirmed that the related art could not be applied to the production of herbicide Fenquinotrione.

For example, as shown in Comparative Example 8, the related art capable of producing a nitroso compound without requiring extreme low temperature did not provide a satisfactory yield when applied to the production of herbicide Fenquinotrione.

INDUSTRIAL APPLICABILITY

According to the present invention, industrially preferred methods for producing a compound of a formula (3) and a compound of a formula (5) are provided. The compound of the formula (3) and the compound of the formula (5), which can be produced by the methods of the present invention, are useful as intermediates for agrochemical and medicine, especially intermediates for herbicide. Further, the methods of the present invention are suitable for production on a large scale such as pilot plant or industrial production. In other words, the methods of the present invention are economical and also environmentally friendly and have high industrial utility value. In sum, the present invention has high industrial applicability.

The invention claimed is:

1. A method for producing a compound of a formula (3), comprising reacting a compound of a formula (1) with a compound of a formula (2) by using a tertiary alcohol and a base:

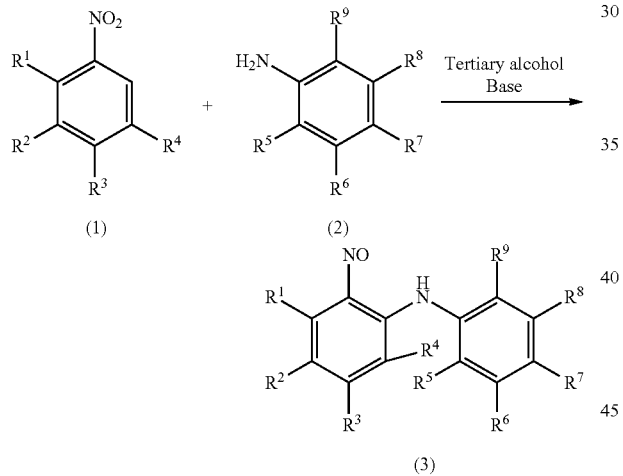

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy, wherein the amount of the base used is 2.0 equivalents to 4.0 equivalents per 1 equivalent of the compound of the formula (2), and the amount of the tertiary alcohol used is 0.3 equivalents to 2.5 equivalents per 1 equivalent of the compound of the formula (2), wherein the base is an alkali metal amide, wherein the reaction is performed in the presence of an aromatic hydrocarbon solvent, and wherein the reaction is performed at 0° C. to 50° C.

2. The method according to claim 1, wherein the reaction of the compound of the formula (1) with the compound of the formula (2) is performed after the tertiary alcohol and the base are each added.

3. The method according to claim 1, wherein an amount of the base used is larger than an amount of the tertiary alcohol used, in terms of equivalents.

4. A method for producing a compound of a formula (3), comprising reacting a compound of a formula (1) with a compound of a formula (2) by using a tertiary alcohol and a base:

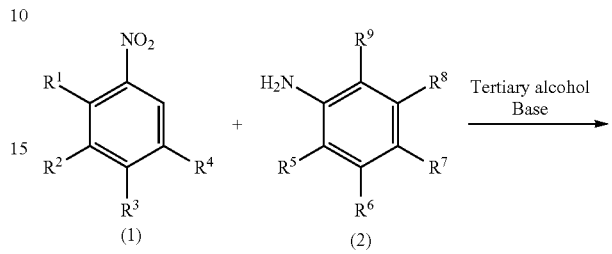

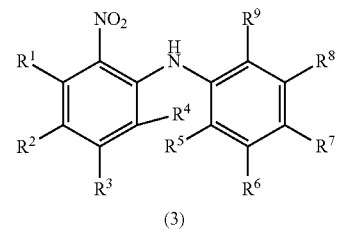

wherein $R^1$, $R^2$, $R^3$, $R^4$, $R^5$, $R^6$, $R^7$, $R^8$, and $R^9$ are each independently a hydrogen atom, a halogen atom, a (C1-C4) alkyl, or a (C1-C4) alkoxy, wherein the amount of the base used is 2.0 equivalents to 4.0 equivalents per 1 equivalent of the compound of the formula (2), and the amount of the tertiary alcohol used is 0.3 equivalents to 4.0 equivalents per 1 equivalent of the compound of the formula (2), wherein the base is an alkali metal hydride, wherein the reaction is performed in the presence of an aromatic hydrocarbon solvent, and wherein the reaction is performed at 20° C. to 70° C.

5. The method according to claim 1, wherein the base is lithium amide.

6. The method according to claim 1, wherein the tertiary alcohol is a compound having the following formula:

wherein $R^{13}$, $R^{14}$, and $R^{15}$ may be the same or different and are each a (C1-C6) alkyl, a (C3-C6) cycloalkyl, a (C2-C6) alkenyl, a (C2-C6) alkynyl, a (C6-C10) aryl, or a (C6-C10) aryl (C1-C4) alkyl, and two selected from $R^{13}$, $R^{14}$, and $R^{15}$ may be bonded to each other to form a ring.

7. The method according to claim 1, wherein the tertiary alcohol is selected from the group consisting of tert-butanol, 2-methyl-2-butanol, 2-methyl-3-buten-2-ol, and 2-methyl-1-phenyl-2-propanol.

8. The method according to claim 1, wherein the reaction is performed at 0° C. to 30° C.

9. The method according to claim 1, wherein
$R^1$ is a hydrogen atom or a chlorine atom;
$R^2$, $R^3$, and $R^4$ are each a hydrogen atom;
$R^5$, $R^6$, $R^8$, and $R^9$ are each a hydrogen atom; and
$R^7$ is a hydrogen atom or methoxy.

10. The method according to claim 1, wherein
$R^1$ is a chlorine atom;
$R^2$, $R^3$, and $R^4$ are each a hydrogen atom;
$R^5$, $R^6$, $R^8$, and $R^9$ are each a hydrogen atom; and
$R^7$ is methoxy.

11. The method according to claim 1, wherein the aromatic hydrocarbon solvent comprises toluene, xylene, chlorobenzene, dichlorobenzene, or a mixture thereof.

12. The method according to claim 4, wherein the base is sodium hydride.

13. The method according to claim 4, wherein the tertiary alcohol is a compound having the following formula:

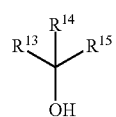

(6)

wherein $R^{13}$, $R^{14}$, and $R^{15}$ may be the same or different and are each a (C1-C6) alkyl, a (C3-C6) cycloalkyl, a (C2-C6) alkenyl, a (C2-C6) alkynyl, a (C6-C10) aryl, or a (C6-C10) aryl (C1-C4) alkyl, and two selected from $R^{13}$, $R^{14}$, and $R^{15}$ may be bonded to each other to form a ring.

14. The method according to claim 4, wherein the tertiary alcohol is selected from the group consisting of tert-butanol, 2-methyl-2-butanol, 2-methyl-3-buten-2-ol, and 2-methyl-1-phenyl-2-propanol.

15. The method according to claim 4, wherein the aromatic hydrocarbon solvent comprises toluene, xylene, chlorobenzene, dichlorobenzene, or a mixture thereof.

* * * * *